United States Patent
Lugaresi

(10) Patent No.: US 9,449,528 B1
(45) Date of Patent: Sep. 20, 2016

(54) GUIDED SYSTEM FOR RESETTING EMBEDDED ANXIOUS AND TRAUMATIC REACTIONS

(71) Applicant: John E. Lugaresi, Waterford, CT (US)

(72) Inventor: John E. Lugaresi, Waterford, CT (US)

(*) Notice: Subject to any disclaimer, the term of this patent is extended or adjusted under 35 U.S.C. 154(b) by 597 days.

(21) Appl. No.: 13/726,176

(22) Filed: Dec. 23, 2012

Related U.S. Application Data

(60) Provisional application No. 61/580,129, filed on Dec. 23, 2011.

(51) Int. Cl.
*G09B 19/00* (2006.01)
*A61M 21/00* (2006.01)

(52) U.S. Cl.
CPC ....... *G09B 19/00* (2013.01); *A61M 2021/0066* (2013.01)

(58) Field of Classification Search
CPC ............................................. A61M 2021/0066
USPC ................. 607/96, 81, 85; 434/236; 600/27
See application file for complete search history.

(56) References Cited

U.S. PATENT DOCUMENTS

| | | |
|---|---|---|
| 2005/0021112 A1 | 1/2005 | Sakamoto |
| 2007/0277304 A1 | 12/2007 | Horinoue et al. |
| 2010/0010371 A1* | 1/2010 | Zayfert et al. ............... 600/558 |
| 2013/0030241 A1* | 1/2013 | Smith ............................ 600/28 |

OTHER PUBLICATIONS

"Post-traumatic stress disorder," retrieved from internet URL http://web.archive.org/web/20090522181716/http://www.nhs.uk/Conditions/Post-traumatic-stress-disorder/Pages/Realstoriespage.aspx on Apr. 29, 2015; wayback machine date of May 22, 2009.*
Michael Lamport Commons, "The Power Therapies: A proposed mechanism for their action and suggestions for future empirical validation", Traumatology: The International Journal for Understanding the Traumatic Processes and methods for Reducing, Preventing, and Eliminating Related Human Suffering, Aug. 2000, vol. VI, Issue 2, Article 5, Florida State University.

* cited by examiner

*Primary Examiner* — Michael Grant
(74) *Attorney, Agent, or Firm* — Bachman & LaPointe, P.C.

(57) ABSTRACT

A method facilitates a participant to reduce or eliminate anxiety over-reactions. A program application is used to collect, assess and store responses from inquiry of said participant's history of significant events. The participant is given a set of directions. The participant is presented with a significant temperature change to said participant's body or a portion thereof for a period of time while using said directions and a means for recording data from sensors or from said participant.

1 Claim, 46 Drawing Sheets

| PHASE \ EMBODIMENT | I | II | III | IV |
|---|---|---|---|---|
| I. DATA ENTRY REVIEW THEME SELECTION AND INSTRUCTION CREATION | GUIDE<br><br>PARTIC-IPANT | GUIDE<br><br>PARTIC-IPANT | GUIDE<br><br>PARTIC-IPANT | GUIDE<br><br>PARTIC-IPANT |
| II. EQUIPMENT SET-UP | PARTIC-IPANT | HOST | HOST<br><br>PARTIC-IPANT | PARTIC-IPANT |
| III. MENTAL PREPARATION VIA MUSIC AND MEDITATION | SKIPPED | PARTIC-IPANT | PARTIC-IPANT | PARTIC-IPANT |
| IV. SYSTEMATIC REVISIT OF PAST SIGNIFICANT EVENTS | GUIDE<br><br>PARTIC-IPANT | PARTIC-IPANT<br>(GUIDE) | PARTIC-IPANT<br>(HOST) | PARTIC-IPANT<br>[(GUIDE)] |
| V. REVIEW OF INTENSE SESSION DATA | SKIPPED | GUIDE<br><br>PARTIC-IPANT | PARTIC-IPANT | GUIDE<br><br>PARTIC-IPANT |
| VI. SESSION FEEDBACK ASSESSMENT | SKIPPED | GUIDE<br><br>PARTIC-IPANT | GUIDE<br><br>PARTIC-IPANT | GUIDE<br><br>PARTIC-IPANT |

PLANNED SESSION: A BLOCK OF TIME WHERE THESE STEPS ARE PERFORMED IN THE SAME DAY OR OVER MULTIPLE DAYS USING THE SAME INSTRUCTION SET.

NOTE: PARENTHESIS, "( )", INDICATE PRESENT OR OPTIONAL ASSISTANT. BRACKETS, "[ ]", INDICATE REMOTE PARTICIPATION.

FIG 1

| ALIAS | PIN | NAME | ALIAS | PIN | NAME |
| --- | --- | --- | --- | --- | --- |
| LCD_SEG1_SEG_5 | 1 | P2[5] | | 26 | |
| LCD_SEG1_SEG_6 | 2 | P2[6] | P80_TUBLVL_1 | 27 | P1[6] |
| LCD_SEG1_SEG_7 | 3 | P2[7] | P80_TUBLVL_2 | 28 | P1[7] |
| | 4 | P12[4] | P80_TUBLVL_3 | 29 | P12[6] |
| | 5 | P12[5] | P80_TUBLVL_4 | 30 | P12[7] |
| | 6 | P6[4] | P80_TUBLVL_5 | 31 | P5[4] |
| CAPSNZ_SCTL_5 | 7 | P6[5] | | 32 | P5[5] |
| CAPSNZ_VABRT_CH_7 | 8 | P6[6] | | 33 | P5[6] |
| CAPSNZ_VABRT_CMOD | 9 | P6[7] | | 34 | P5[7] |
| | 10 | VSSB | USBFS_1_DPOS | 35 | P15[6] |
| | 11 | IND | USBFS_1_DNEG | 36 | P15[7] |
| | 12 | VB | | 37 | VDDD |
| | 13 | VBAT | | 38 | VSSD |
| | 14 | VSSD | | 39 | VCCD |
| | 15 | XRES_N | | 40 | N/C |
| LCD_SEG1_COM_0 | 16 | P5[0] | | 41 | N/C |
| LCD_SEG1_COM_1 | 17 | P5[1] | | 42 | P15[0] |
| LCD_SEG1_COM_2 | 18 | P5[2] | | 43 | P15[1] |
| LCD_SEG1_COM_3 | 19 | P5[3] | CAPSNZ_SCTL_0 | 44 | P3[0] |
| | 20 | P1[0] | CAPSNZ_SCTL_1 | 45 | P3[1] |
| | 21 | P1[1] | CAPSNZ_SCTL_2 | 46 | P3[2] |
| | 22 | P1[2] | CAPSNZ_SCTL_3 | 47 | P3[3] |
| | 23 | P1[3] | CAPSNZ_SCTL_4 | 48 | P3[4] |
| CAPSNZ_VABRT_CH_1 | 24 | P1[4] | | 49 | P3[5] |
| CAPSNZ_VABRT_CH_0 | 25 | P1[5] | | 50 | VDDIO3 |

FIG. 21

| ALIAS | PIN | NAME | ALIAS | PIN | NAME |
|---|---|---|---|---|---|
| P8_LMIC | 51 | P3[6] | | 76 | P0[4] |
| P9_LWATERLVL | 52 | P3[7] | | 77 | P0[5] |
| P10_TUB_ENTRY | 53 | P12[0] | | 78 | P0[6] |
| P70_TEMP_0 | 54 | P12[1] | | 79 | P0[7] |
| P71_TEMP_1 | 55 | P15[2] | P1_PHASE_2 | 80 | P4[2] |
| P72_TEMP_2 | 56 | P15[3] | P1_PHASE_3 | 81 | P4[3] |
| | 57 | N/C | P1_PHASE_4 | 82 | P4[4] |
| | 58 | N/C | P1_PHASE_5 | 83 | P4[5] |
| | 59 | N/C | | 84 | P4[6] |
| | 60 | N/C | | 85 | P4[7] |
| | 61 | N/C | | 86 | VCCD |
| | 62 | N/C | | 87 | VSSD |
| | 63 | VCCA | | 88 | VDDD |
| | 64 | VSSA | P50_PHASE4A | 89 | P6[0] |
| | 65 | VDDA | P50_PHASE4B | 90 | P6[1] |
| | 66 | VSSD | P50_PHASE4C | 91 | P6[2] |
| | 67 | P12[2] | P50_PHASE4D | 92 | P6[3] |
| | 68 | P12[3] | P50_PHASE4E | 93 | P15[4] |
| P1_PHASE_0 | 69 | P4[0] | P55_PHZ4_DRYWET | 94 | P15[5] |
| P1_PHASE_1 | 70 | P4[1] | LCD_SEG1_SEG_0 | 95 | P2[0] |
| CAPSNZ_VABRT_CH_2 | 71 | P0[0] | LCD_SEG1_SEG_1 | 96 | P2[1] |
| CAPSNZ_VABRT_CH_3 | 72 | P0[1] | LCD_SEG1_SEG_2 | 97 | P2[2] |
| CAPSNZ_VABRT_CH_4 | 73 | P0[2] | LCD_SEG1_SEG_3 | 98 | P2[3] |
| CAPSNZ_VABRT_CH_5 | 74 | P0[3] | LCD_SEG1_SEG_4 | 99 | P2[4] |
| CAPSNZ_VABRT_CH_6 | 75 | P0[4] | | 100 | VDDIO2 |

FIG. 22

| TYPE | NAME | DOMAIN | DESIRED FREQUENCY | NOMINAL FREQUENCY | ACCU-RACY (%) | DIVIDER | START ON RESET | SOURCE CLOCK |
|---|---|---|---|---|---|---|---|---|
| SYSTEM | DIGITAL_SIGNAL | DIGITAL | ?MHZ | ?MHZ | +/-0 | 0 | | |
| SYSTEM | XTAL_32KHZ | DIGITAL | 32.768KHZ | ?MHZ | +/-0 | 0 | | |
| SYSTEM | XTAL | DIGITAL | 33.000KHZ | ?MHZ | +/-0 | 0 | | |
| SYSTEM | ILO | DIGITAL | ?KHZ | 100.000KHZ | +/-20 | 0 | X | |
| SYSTEM | BUS_CLK | DIGITAL | ?KHZ | 24.000MHZ | +/-4 | 1 | X | MASTER_CLK |
| SYSTEM | MASTER_CLK | DIGITAL | ?KHZ | 24.000MHZ | +/-4 | 1 | X | PLL_OUT |
| SYSTEM | PLL_OUT | DIGITAL | 24KHZ | 24.000MHZ | +/-4 | 0 | X | IMO |
| SYSTEM | IMO | DIGITAL | 24KHZ | 24.000MHZ | +/-4 | 0 | X | |
| SYSTEM | USB_CLK | DIGITAL | 48KHZ | 48.000MHZ | +/-4 | 1 | X | IMOX2 |
| LOCAL | LCD_SEG1_INT_CLK | DIGITAL | 132.096KHZ | 131.868KHZ | +/-4* | 182 | X | AUTO:MSTR_CLK |
| LOCAL | CAPSNZ_CNTLS_CLK | DIGITAL | 12.000MHZ | 12.000MHZ | +/-4* | 2 | X | AUTO:MSTR_CLK |
| LOCAL | CAPSNZ_VABORT_CLK | DIGITAL | 12.000MHZ | 12.000MHZ | +/-4* | 2 | X | AUTO:MSTR_CLK |
| LOCAL | LCD_SEG1_CLK_1 | DIGITAL | ?MHZ | 24.000MHZ | +/-4 | 0 | X | BUS_CLK |

NOTE:*TOLERANCE +/-5%

FIG. 23

| RANDOM 6 DIGIT PROFILE | 1. (OR) 2. | PRIOR ID | AGE | DOBIRTH |
|---|---|---|---|---|
| ☐ CLICK 2X FOR NEW | 1.A) CREATE PROFILE  CLICK ID TO LOAD | 96858 | 47 | 7/17/1962 |

96858

3. FILL IN DATA

FROM 1.A) OR 2.
A) ☒ MALE
DATE ADOPTED: B) DOB: 7/17/1960  AGE: 47
ADOPTED ☒ SEPARATED ☐
PARENTS ☒
SIBLINGS ☐  NO. SIBLINGS 4

FAMILY MEMBERS  DOB: 7/17/1962  FAMILY- DOB
(SHARING MEALS)  DAD 1920
FIRST/NICK NAME: ☐ ⇒  MOM 1928

ARE YOU A PARENT? ☐ ☐ FEMALE ☐ 4 NO. KIDS

DATE OF EVENTS

Jul 1962  | Jul ▶ | 1962 ▶

| Sun | Mon | Tue | Wed | Thu | Fri | Sat |
|---|---|---|---|---|---|---|
| 1 | 2 | 3 | 4 | 5 | 6 | 7 |
| 8 | 9 | 10 | 11 | 12 | 13 | 14 |
| 15 | 16 | 17 | 18 | 19 | 20 | 21 |
| 22 | 23 | 24 | 25 | 26 | 27 | 28 |
| 29 | 30 | 31 | | | | |

| DOB |   |
|---|---|
| 10 | 1 |
| 20 | 2 |
| 30 | 3 |
| 40 | 4 |
| 50 | 5 |
| 60 | 6 |
| 70 | 7 |
| 80 | 8 |
| 90 | 9 |

4. HISTORY

2X CLICK EACH ITEM

PERSONAL AILMENTS
MEDICAL DIAGNOSIS
FAMILY DIAGNOSIS

5. SCOPE

INTIMACY/RELATIONS
SLEEP
WORK
RECREATION
SELFMEDICATION
PHYSICAL HEALTH

6. EVENTS

EARLY MEMORIES
FAMILY AFFECTION
FAMILY RULES
FAMILY BEHAVIOR
MOOD EXPLORATION
SEXUAL DEVELOPMENT

FIG. 26

| MULTIPLE SCLEROSIS ☐ | STROKE ☐ | HYPER-TENSION ☐ | GLAUCOMA ☐ | NIGHT BLINDNESS ☐ | BURNING MOUTH ☐ |
|---|---|---|---|---|---|
| ANXIETY ☒ | DEPRESSION ☒ | ALLERGIC RHINITIS ☐ | POST PARTUM DEPRESSION ☐ | NIGHT BLINDNESS ☒ | CHRONIC SINUSITIS ☒ |
| MULTIPLE SCLEROSIS ☐ | AUTISM ☐ | HYPER-TENSION ☐ | OBSESSIVE COMPULSIVE ☐ | ALZHEIMER'S ☐ | ADD ADHD ☒ |

WHAT, WHERE DOES IT HURT?
CIRCLE AREA, NUMBER AND ADD COMMENTS.
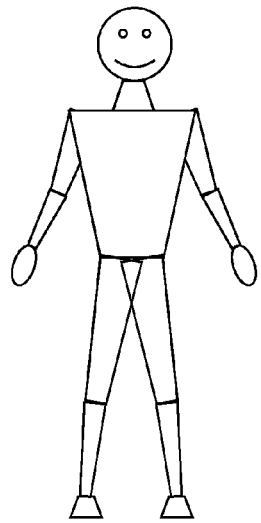
FRONT
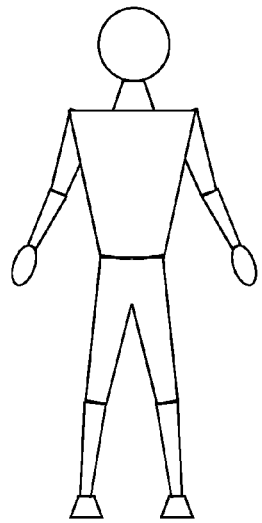
BACK
INJURIES, BREAKS, HOSPITAL VISITS
CAR, BICYCLE ACCIDENTS OR SIMILAR.
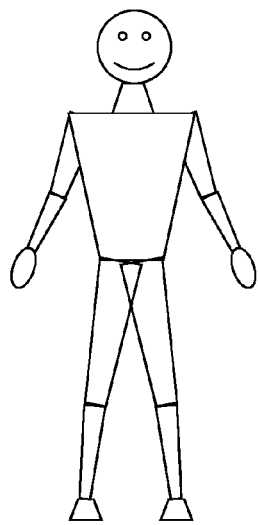
FIG. 37

FIG. 44A

ACCIDENTS/SURGERIES

Ever have other small surgeries where you did spend a night or more in the hospital?

As an adult, what type of auto accidents did you have? Do you remember by yourself or through family members sharing the story? Photos?
Did you ever fallen down and get tested for unconsciousness?
Just prior or during your (sports injuries or) accident, did you ever get a vision or image that helped or warned of impending injury, harm or escape by reacting to the image?

Just prior or during your (sports injuries or) accident, did you ever get a verbal, imagined or conscious (guiding voice) message that helped or warned of impending injury, harm or escape by reacting to the message?
During or just after your (sports injuries or) accident, did you ever forget details of the event or short durations?

Up to 24 hours after your injury or accident, did you have difficulty thinking?

Up to 24 hours after your accident, did you have memories of intense pain? Also, were you on pain relieving drugs?

Was your pain apparently delayed like 48 - 72 hours after the accident/injury?
Ever have an 'out-of-body' experience where you were looking down or at yourself from a distance?

As an adult, what type of severe sports accidents did you have? Do you remember by yourself or through family members sharing the story? Photos?

Ever have other surgeries where you did not stay overnight in the hospital?
Do you recall pre-operative stress, anxiety or fear?
Have you ever been treated for a terminal illness or condition?
Has an immediate family member or loved one ever been treated for a terminal illness or condition?

As a pre-teen, what type of severe sports accidents did you have? Do you remember by yourself or through family members sharing the story? Photos?

As a child, what type of severe sports accidents did you have? Do you remember by yourself or through family members sharing the story? Photos?
Ever have your tonsils removed?

FIG. 44B

CHILD DEVELOPMENT

Did you grow up in an environment that made you feel neglected from food, physical or emotional support? (i.e., not knowing when food would come, or thinking you needed to hide from some body, receiving poor quality or quantity of food than other siblings)

Before the age of 17, did you experience the wrath of bullying or prolonged exposure to one?

Before the age of 12, did you experience or witness sexual abuse, verbal abuse, physical abuse, or domestic violence?

Did you grow up in an environment that seemed unsafe or unstable? (i.e., not knowing when food would come, or thinking you needed to hide from some body)

As a pre-teen, did you experience separation from parent emotionally or through divorce?

Before the age of 12, did you experience serious illness or have medical procedures (i.e., surgeries, intrusive testing procedures, radiation, etc)?

DEPRIVATIONS/INDULGENCES

Do you restrain yourself from sexual feelings and desires?

Do you use drugs or alcohol to ease your pain?

Do you engage in S&M or B&D sexual activities?

Do you withhold your favorite foods as a punishment or discipline for weight control?

Do you harm yourself?

Do you reward yourself with your favorite foods excessively or frequently?

Do you have sex to enjoy the pleasure of having the sex rather than the act expressing intimacy with your partner?

EVENTS OF PTSD

Did you witness in close proximity Natural disasters, car crashes, medical surgeries, or plane crashes?

Have you witnessed first hand and in close proximity Sexual abuse, physical abuse, violence, kidnapping or rape?

Have you ever participated or observed a war zone up close? (Include urban drive-by and high gun shooting zones)

Ever have ideas about committing suicide?

FIG. 44C

MENTAL HEALTH
    Do you get to feelings of hopelessness easily or for long periods of time?
    Ever attempt or act out suicide? (i.e., cutting one's self, acting dangerously, dangerous sports where death or serious injury is possible)
    Have you ever prepared to commit suicide? (i.e., preparing plans or taking actions to implement plans)
    Have you ever intentionally injured your self?
    Are you in a time in your life where suicide may be an option?
    Do you get to feeling guilt, shame or self-blame easily, frequently or for long periods of time?
    Do you get depressed easily or for long periods of time?

PHYSICAL HEALTH CONDITIONS
    Do you have problems with digestion? Included are irritable bowel syndrome (IBS), Crohn's disease, acid reflux, etc.
    Do you get migraine or regular headaches often?
    Do you get chest pains?

RECREATION
    Do you engage in any high risk sports? (i.e., motor car/boat racing, bungee jumping, parachuting, boxing, extreme fighting, etc)

RELATIONSHIPS/INTIMACY
    Do you engage in risky sexual behavior? (i.e., multiple and/or casual sexual partners without condoms, one night stands, BD/SM)
    Do you witness or experience domestic violence or abuse?
    When with others do you have feelings of mistrust and betrayal often?
    Do you ever feel alienated and alone frequently or for long periods of time?

SELF MEDICATION
    Do you use mind altering activities to improve your mood? (i.e., sex, dancing, music, shopping and working excessively.) The feelings you dislike are most likely have gotten you into more distracting activity and trouble than it was intended to fix.
    Do you use mind altering substances alcohol or drugs to improve your mood? Drugs or alcohol may interfere with your normal relationships/work.
    Do you use anger to improve your mood? Or feel anger's power to frequent the habit or pull towards it as a usual response.

SLEEP
    Do you wake up frequently due to reasons other than night mares?
    Do you regularly have trouble sleeping soundly for 6-8 hours?
    Do you wake up frequently due to night mares?

WORK
    Do you regularly work more than 40 hrs per week for your profession without additional compensation?
    Do you regularly work more than 40 hrs per week for your profession?

FIG. 45A

EARLY MEMORIES
    What was your earliest memory with your Father, Dad?
    When you were very young did you favor one sibling more than the another?
    Did you have any bad memories with your favored sibling?
    When you were almost a teen which brother/sister did you favor?
    Did you have any bad memories with your Brother, Ben?
    Did you change affections toward other siblings? How, so?
    When did the family assemble in greatest numbers as a unit? (before elders left/married)
    What was your earliest memory?
    What was your earliest memory with your Mother?
    What was your earliest memory with your brother, Dave?
    What was your earliest memory with your brother, Joe?
    What was your earliest memory with your brother, Ben?
    Did you have any bad memories with your sister, Jessie?
    Did you have any bad memories with your brother, Jerry?
    Did you have any bad memories with your brother, Ted?
    Did you have any bad memories with your Father?
    What was your earliest memory with your sister, Jessie?
    Did you have any bad memories with your Mother?

FAMILY AFFECTION
    How regularly did your siblings express love/affection to you?
    How frequently did your parents show passion, by kissing, in front of the family?
    How often did your parents show love their children?
    How frequently did your parents argue?
    How regularly did your Mother express love/affection to you?
    How regularly did your Father express love/affection to you?
    How frequently did your parents show passion, by holding hands, in front of the family?
    How frequently did your parents show passion, by hugging, in front of the family?
    How frequently did your parents show passion, by dating?

FAMILY BEHAVIOR
    Your Mother's mood can be described by you as:
    Moods were changed by siblings:
    Moods were changed by Father:
    Moods were changed by Mother:
    Your sibling's can be described by you as:
    Your Father's can be described by you as:

FIG. 45B

FAMILY RULES
    What were the family rules or behaviors when somebody was being loved?
    What were the family rules or behaviors when somebody was angry?
    What were the family rules or behaviors when somebody was happy?
    What were the family rules or behaviors when somebody was depressed?
    What were the family rules or behaviors when somebody as a toddler was naked?
    What were your family food/table rules?
    What were the family rules or behaviors when somebody as a pre/teen was naked?
    What were the family rules or behaviors when somebody was sad?

MOOD EXPLORATION
    What did you do for fun and excitement?
    How were your moods were experienced? (i.e., quickly, slowly, easily, quietly, inwardly only)
    How were Mother's moods were experienced?
    How were Father's moods were experienced?
    How were siblings Moods were experienced? (i.e., quickly, slowly, easily, quietly, inwardly only)
    What did you do to relax?
    Do you use drugs or alcohol to improve or alter your mood?
    Some friends ask you to join them to play one of your fun activities, depending upon your mood you would _____

OTHER SIGNIFICANT MEMORIES
    Describe another event where you had a traumatic memory never forgotten.
    Describe another event where you had a difficult memory.
    Describe another event where you had a forgotten and recalled traumatic memory.
    Describe another event where you had an exciting memory.
    Describe another event where you had a fun or fond memory.
    Describe another event where you had a lesson learned.
    Describe another event where you had a critical story.
    Describe another event where you had hurt feelings.
    Describe another event where you had a strong memory.
    Describe another event where you had a scary memory.
    Describe another event where you had an early memory.
    Describe another event where you had an accident.

PARENTAL GUIDANCE
    Were there certain things you could not allow your parents to know for fear of punishment or lack of their approval?
    What methods did your parents use for discipline?
    Ever hid cigarettes, drugs or sexual paraphernalia from your parents?

FIG. 45C

SEXUAL DEVELOPMENT
> What was your longest intimate relationship as an adult?
>
> What was your longest intimate relationship as a pre/teen?
>
> Do you feel as if you have missed many opportunities to connect intimately (having at least dating status) with the opposite sex?
>
> If you played the anatomy exploration game "I'll show you mine if you show me yours." explain the details.
>
> When did you see your first pornographic magazine or video?
>
> When was your first lover's kiss with the opposite sex?
>
> When did have your first intimate boy/girl friend? (puppy love pre-teen)
>
> When and how did you understand the differences between the sexes?
>
> How was your first sexual exploration with the opposite sex?
>
> What were your sources of knowledge of the opposite sex?

SOCIALIZING
> On average, during college years, with how many adults did you regularly associate of the opposite sex in a non-sexual manner?
>
> On average, during pre-teen years, with how many siblings did you regularly play?
>
> On average, during teen years, with how many peers/siblings did you regularly play?
>
> As an adult, on average, with how many peers do you regularly associate?
>
> For pre-teen years, how many close friends did you normally have?
>
> For teen years, how many close friends did you normally have?
>
> For 20/30 something years, how many close friends did you normally have?
>
> Was it easy for you to trust your friends?
>
> How frequently did your friends betray your trust?
>
> When friends betrayed your trust, your likely reactions were:
>
> How long did you know your best friend?
>
> As a pre-teen how many adults could you approach to talk about a troubling issue that you could not or dared not talk about with your parents?
>
> You are invited to join a good friend to a house party where you will only know your friend. When you arrive your friend makes a few introductions and excuses him/her-self. You ...
>
> Some friends ask you to join them to play one of your fun activities, you ...
>
> On average, during college years, with how many peers/siblings did you regularly associate?

FIG. 46

- Make 4-5 hour appointment with host site for a 108+ degree Fahrenheit session
- Bring comfortable bathing suit, digital instrumental meditation music, towels, wash cloths, bag
- Your themes are:
- Sadness and feeling lonely per
  - Break up with Mark Q
  - Jeff X
  - Lonely feeling searching for universities
  - Joey break up
- Stressed
  - Mother wanting me to date after breaking up with Mark
  - Parents separating
  - Fitting in at campus
  - Roommate tension with Beth
  - Career dilemma
  - Fighting with Joey
  - Sneaking to be w/ Joey; Mom insists on chaperoned dating
  - Fighting mom regarding style of dress
  - Losing classmates in crash
- Sexuality and expression
  - With Mark Q at university
  - With Jeff X in Junior/Senior year
  - With Rick in Sophomore year
  - With Joey after then before dating when competing for him at camp
  - Losing top swimming near suitor
  - Kissing Bobby
- At the appointment meditate upon one them and its items in order shown with digital instrumental music you provide (MP3, wav, CD, etc)
- Host will provide room set-up with equipment to play music and upload instructions while you meditate
- Get into tub and expose most of body to the hot (not scalding) water as you nearly lie, in seated position and head submerged positions for a minute or three
- Get in the heated tub and continue to relive the first item of theme 1 as prompted and check off when emotions are released for that item
- Interface will prompt the next item or advise a rest period out of the tub for a number of minutes
- Repeat as many items in the first theme in about 1 hour, if done before the hour is up then the next theme and its first item will be queued up until the maximum time limit is reached
- Rest an additional 10-50 minutes before returning to regular daily activities
- Review recordings of your revisited items at a later time preferably within 48 hours
- Upload recordings or portions thereof to the Guide for assessment
- Receive feedback and/or new instruction sets for your next session

GUIDED SYSTEM FOR RESETTING EMBEDDED ANXIOUS AND TRAUMATIC REACTIONS

CROSS-REFERENCE TO RELATED APPLICATION

Benefit is claimed of Ser. No. 61/580,129, filed Dec. 23, 2012, and entitled "Guided System for Resetting Embedded Anxious and Traumatic Reactions", the disclosure of which is incorporated by reference herein in its entirety as if set forth at length.

BACKGROUND OF THE INVENTION

For centuries soldiers have suffered from traumatic stress, which in early years went by names of shell shock during World War I, and "acute mania" in the American Civil War. It was the Vietnam veterans return home and commonality of symptoms with rape victims that lead to the more recent and common understanding of post-traumatic stress disorder (PTSD) and associated symptoms.

The funding for veterans pushes research into greater understanding of the effects of the emotional trauma suffered by soldiers and victims alike. Much is known about the body's physiological processes during the fight/flight/freeze responses. However, they will not be covered in medical detail regarding the central nervous system responses when in trauma. One worth mention has been called "general adaptation syndrome", which entails the same or similar processes that manifest in physical and/or emotional reactions during an original traumatic event. These trauma responses include over-reactions to stimuli, sleepless nights, headaches, outbursts of anger, night-mares of terror or recurrent negative themes slowly deteriorate the quality of life for those affected. Depression and suicide or resigning from normal activities is still common among PTSD sufferers and especially high in the soldier grouping. However, current treatments seem exhausting and/or ineffective, and diminishing health and morale continue chronically.

Medical providers and governments were and are still at a loss of how to treat the afflicted. The symptoms were observable that something was amiss. But, especially for soldiers the wounds did not seem to merit a bandage or an operation. General Patton had even accused soldiers, of presenting these symptoms as a lack of being strong soldiers—attempting to evade their duties. Also, early treatments, which included electric shock therapy, electric heat baths, milk diets, hypnotism and mechanical devices to force realignment of body structures (usually limbs) were ineffective. So, soldiers were given some recuperation time and if able-bodied were sent back to the lines. Even though, these soldiers had physiological responses that are now becoming understood and associated to PTSD—effects common in combat soldiers.

Modern therapeutic techniques typically take months to be effective. Prolonged exposure therapy (PE) is a cognitive behavioral technique that exposes the patient to traumatic memories both in and out of therapy for extended time periods, typically eight to twelve weeks. Each week they attend one or two intensive therapist sessions revisiting the traumatic events lasting about an hour. During the multiple week PE program the patient is directed to further expose oneself to similar emotional trauma.

Power therapies (including eye movement desensitization and reprocessing (EMDR), emotional freedom techniques, thought field therapy (TFT), traumatic incident reduction (TIR), visual-kinetic dissociation (V-KD) and tapas acupressure techniques that have come to public attention through alternative medicine) deal with methods contrary to this invention. EMDR is a reprogramming procedure using a therapist and eye movements directed by the therapist. Each of these methods utilizes highly trained therapists and scheduled appointments outside of the patient's home. TFT is a tapping of specific acupressure meridians, while engaging in thought about prior traumatic events. TIR, according to Wikipedia, is a form of psychotherapy in which a technique is used to assist a patient suffering from post-traumatic stress disorder by re-living the experience in a controlled environment, again repeating, with a counselor, therapist or psychotherapist. V-KD seems to be related to the Neuro-Linguistic Programming studied by its founders John Grinder and Richard Bandler, which "involves temporarily induced dissociation from the negative feelings associated with traumatic memory through visual review of the traumatic event(s) from a different perspective". Michael Lamport Commons, "The Power Therapies: A proposed mechanism for their action and suggestions for future empirical validation", Traumatology: The International Journal for Understanding the Traumatic Processes and methods for Reducing, Preventing, and Eliminating Related Human Suffering, Vol. VI, Issue 2, Article 5, Florida State University, August, 2000.

Another art is that of saunas. Finnish saunas typically involve temperatures of 180-212 degrees Fahrenheit with several heating and cooling cycles that could last 30 minutes to several hours. Cooling cycles are usually taken as personally desired.

Other heat-related observations have been made in published findings. Heat shock proteins (HSPs) play a role in stress conditions from inflammation, exercise, oxygen deprivation, cell exposure to toxins or ultraviolet light, and from brief cellular exposure to sub-lethal high temperatures. U.S. patent application Ser. No. 11/527,468 (PGPub. 20070277304) contains a design for a modern bathing chamber which monitors both water and patient internal temperatures where the desired temperature is 108.5 degrees Fahrenheit. The purpose is to minimize stresses and provide a longer experience to counteract the HSPs and the associated stress upon the patient. Another similar example is U.S. patent application Ser. No. 10/500,202 (PGPub. 20050021112). It attempts to alleviate patient HSP response to a comfortable level by use of music, colored light and/or combinations with facial cooling or anesthesia.

SUMMARY OF THE INVENTION

This guided system may help return anxious victims to a state of health of normal functioning. This guided system may mitigate the uncontrollable nature of these progressively worsening deeply embedded symptoms.

The present system is a systematic procedure intended to reduce and even eliminate anxiety over-reactions. A guide elicits a patient's past significant events, scales them to the patient's significance, correlates themes and past events to the symptoms to diminish, and creates, with the aid of a computer program, a set of instructions (directions) for the patient to follow. The patient uses a device to follow the instructions while it measures criterion, namely the application of an external significant temperature difference to the patient's body or part thereof, as the patient recalls the specific past events called out by the instructions as well as recording the patient. Depending upon the embodiment, the guide and, optionally, the patient review the data from the data intake, the reactions from the significant temperature change, and data collected to evaluate the patient's response. The guide gives feedback and creates a new instruction set to further reduce undesired symptoms.

Accordingly, one aspect involves a method facilitates a participant to reduce or eliminate anxiety over-reactions. A program application is used to collect, assess and store responses from inquiry of said participant's history of significant events. The participant is given a set of directions. The participant is presented with a significant temperature change to said participant's body or a portion thereof for a period of time while using said directions and a means for recording data from sensors or from said participant.

BRIEF DESCRIPTION OF THE DRAWINGS

FIG. 1 is a table of four embodiments and the roles in each stage.

FIGS. 20 to 22 are a schematic representation of a possible pin layout of the selected microcontroller.

FIG. 23 is a table of clock signals for a microcontroller.

Figure 29:
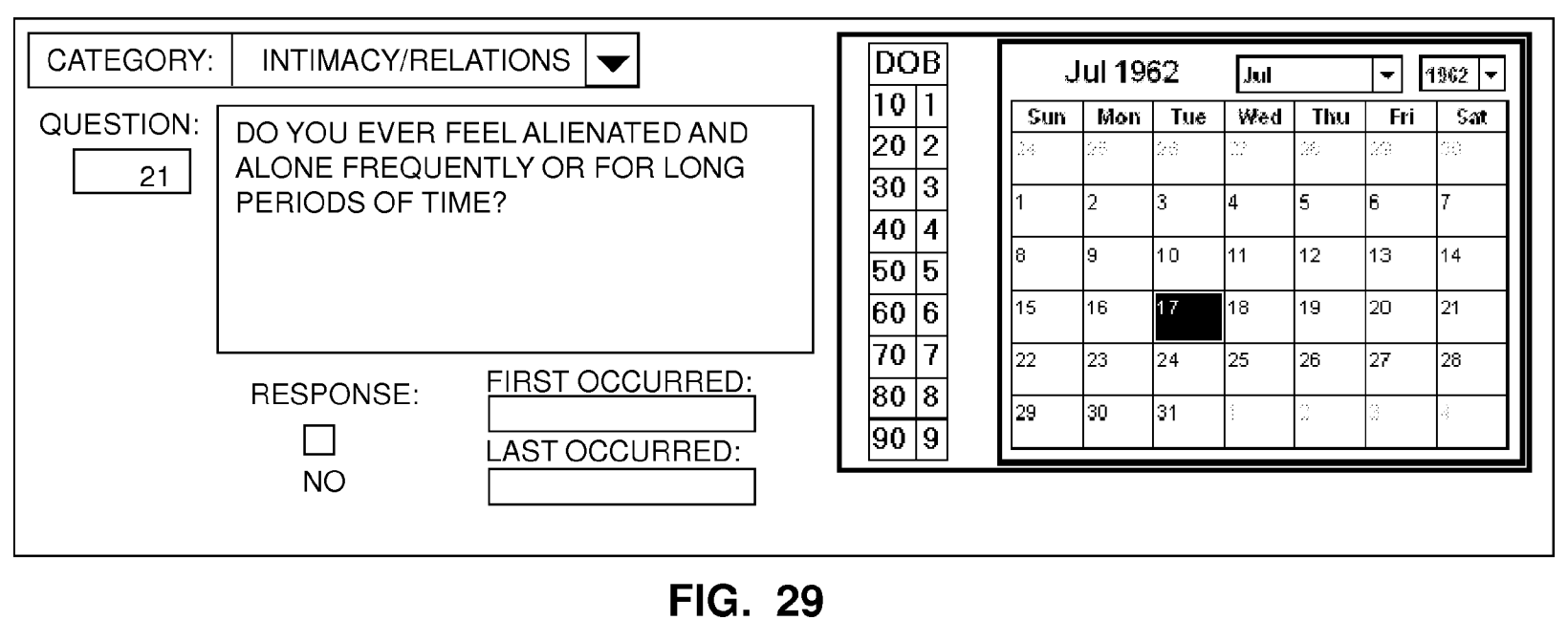
Figure 30:
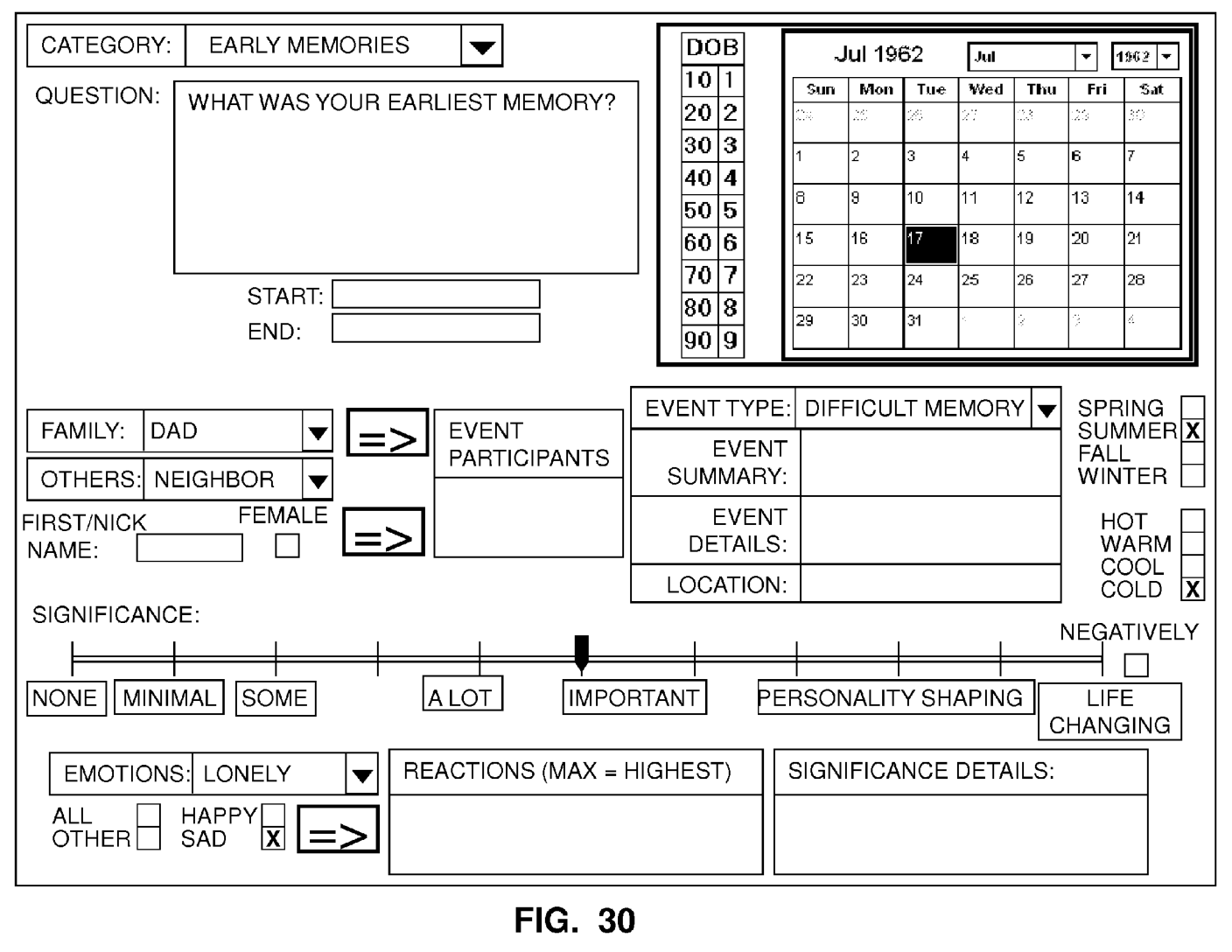

FIGS. 25 to 31 are a series of application graphical user interface screens for gathering data from patient.

FIG. 37 is a blank worksheet the application may print for the patient to fill out.

FIGS. 44A, 44B and 44C are a first patient questionnaire.

FIGS. 45A, 45B and 45C are a second patient questionnaire.

FIG. 46 is a view of an instruction set.

DETAILED DESCRIPTION

Figure 2:
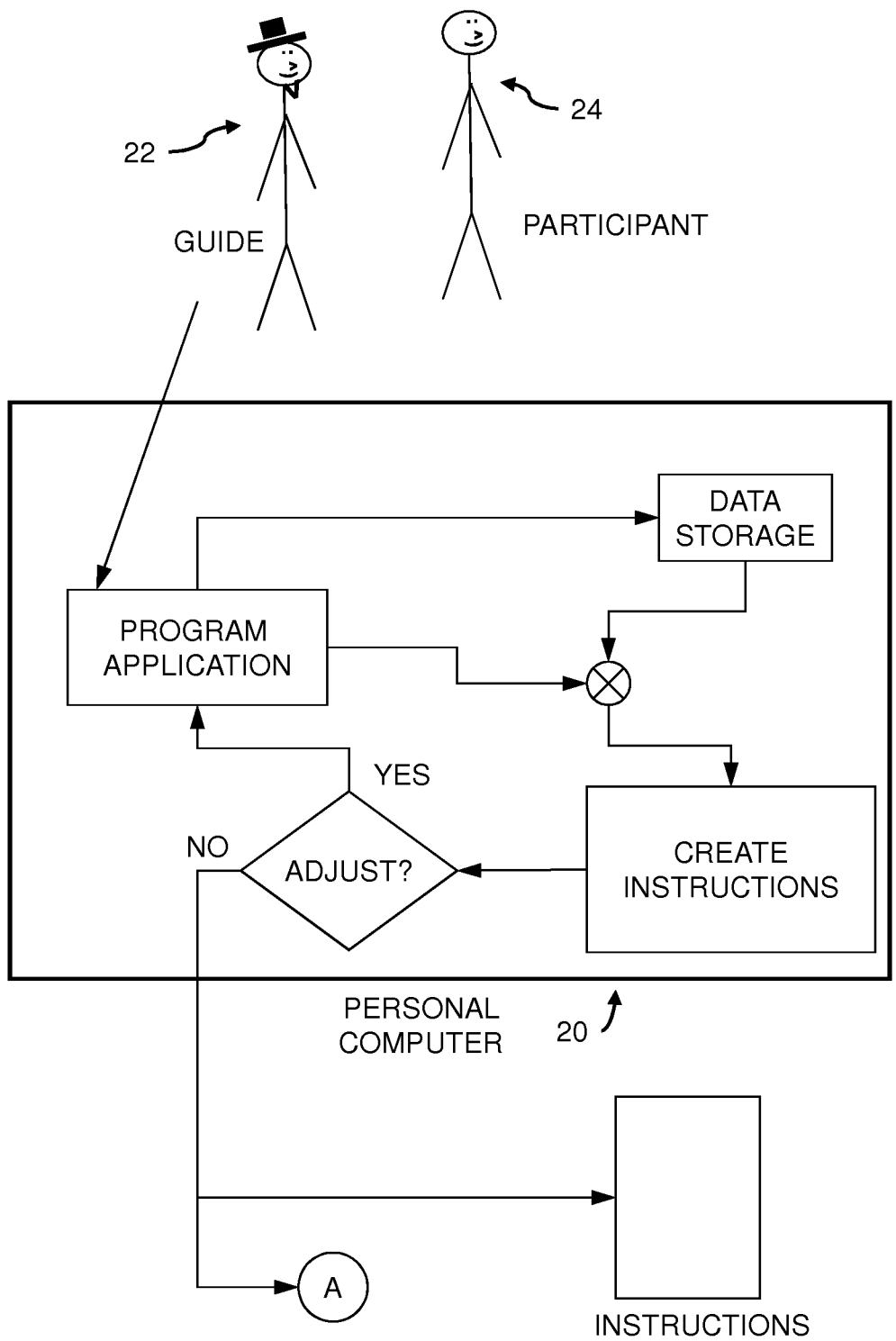
FIGS. 2 and 3 are a flowchart of the first embodiment with a guide and patient.
Figure 3:
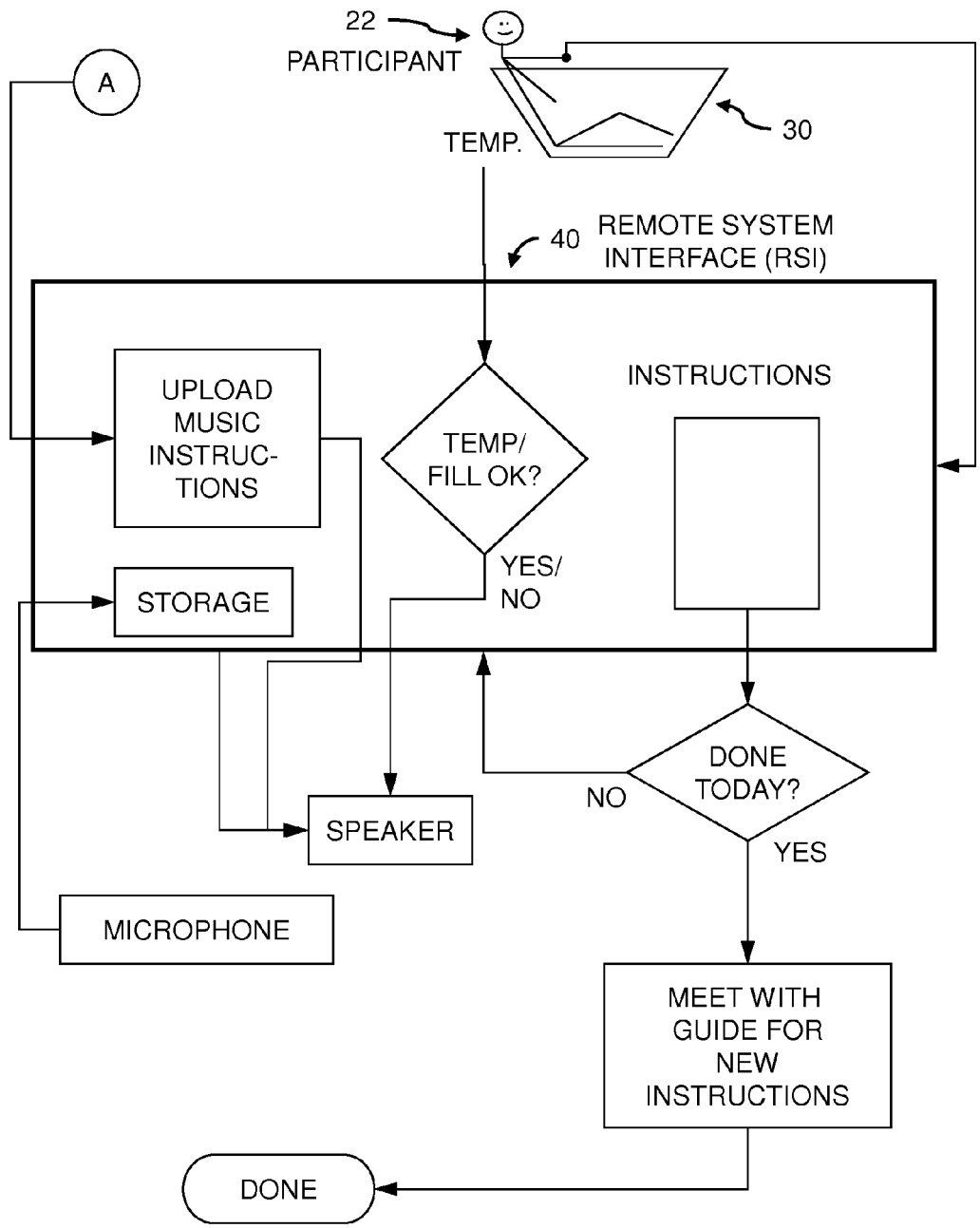

The first embodiment in FIGS. 2 and 3 includes a device 20 (e.g., a personal computer (PC)) which stores information gathered by a guide (e.g., a therapist) 22 from a participant (patient) 24. A graphical user interface (GUI), on the PC may prompt the guide to obtain information from the patient and allow the guide to enter the information back into the PC.

The guide and a program application (e.g., on the PC) create a set of instructions for the patient to carry out at a later time. At such later time, patient carries out the instructions which include use of elevated temperature therapy involving a warm or hot bath (e.g., in tub 30 of FIG. 3). To carry out the instructions, the patient uses a device designated a "remote system interface" 40 (RSI) (e.g., a touch-screen or other electronic input/output device) that interfaces with the patient and, preferably, with the tub. In the following example, guide actions may be prompted by the PC.

Figure 27:
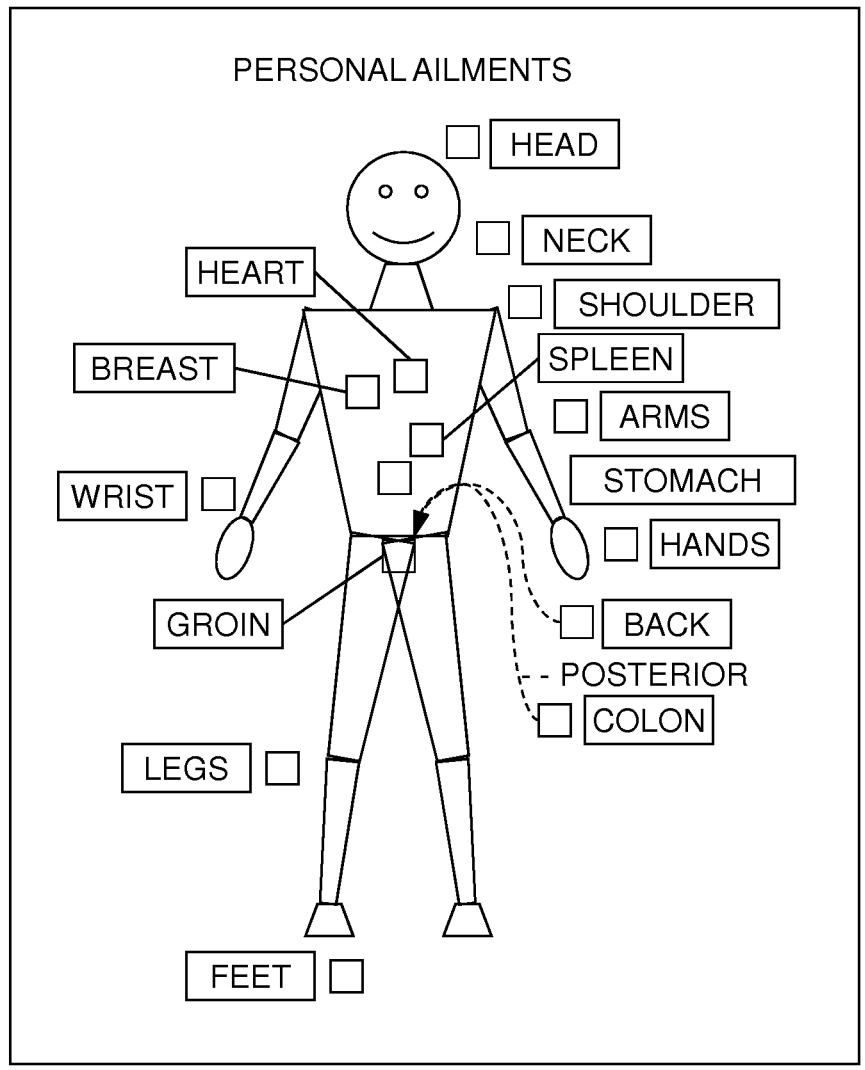

Embodiment I Part 1 a. Guide asks patient for date of birth (DOB) and enters the date of birth by manual entry or calendar entry. The GUI prompts the guide to obtain from the patient information about gender and family environment which the guide then enters into the GUI (FIG. 26). For example, the prompted data may include parents' marital status, dates marital status changed, the number of siblings, family members' DOB, patient's wedding date, patient's children's DOB, if any, and the total number of patient's children. The collected family data is stored in the PC.

b. After collecting family data, a medical history of the patient is requested and entered by the guide into the PC. On the GUI, a further menu (FIG. 27) is opened (e.g., by double-clicking the word "personal ailments" in FIG. 26). The ailments relating to each body part such as the head are made available as a series of check boxes (FIG. 28) (e.g., when checked and selecting the word "head" in FIG. 27). The GUI prompts (not shown) the guide to make entries of prior medical diagnosis provided by the patient. For example, irritable bowel syndrome check box (not shown) may be checked when the stomach menu was opened (e.g., by double clicking the word "stomach" in FIG. 27). The GUI prompts the guide to collect and enter patient family medical history. For example, patient may be asked medical history about patient's parents, aunts, uncles and grandparents. Details are not shown but are similar to the two GUI forms of FIGS. 27 and 28 modified to collect this family history.

c. The guide similarly obtains and enters information regarding the patient's emotional environment (e.g., see section 5 of FIG. 26). To do this the guide may open another GUI menu (FIG. 29) (e.g., by double-clicking the word "intimacy/relations" FIG. 26) and present the commonly themed questions. The guide records the patient's response. For a yes response, start and finish dates are entered; these yes responses and their dates are later used to match/correlate related significant events. The guide enters data for all categories (e.g., from section 5 of FIG. 26) using said menu (FIG. 29). For example, these categories may cover patterns of sleep, work, recreation, self-medication, physical health, PTSD, deprivations/indulgences, accidents/surgeries and child development.

d. Guide, prompted by the GUI, asks patient for a series of specific past significant events (FIG. 30). For each event (e.g. type selectable via pulldown or other menu), the guide enters: an event summary; details highlighting the event; and a location description. The GUI prompts the guide to request details of the event including persons at the event (e.g., by pulldown). A people list is built using one or more pulldown people selections. Guide continues to select a season when event occurred (e.g., by check box). The temperature experienced by the patient (e.g., simple check boxes for cold/cool/warm/hot or other entry and storage method and form) is selected/entered. This temperature may be utilized later to facilitate re-living of the particular event.

e. The story of the event is entered with details that made it important. The guide assigns a value for the event significance (e.g., via a menu slider on the GUI by placing the slider on best matching descriptor for the event (FIG. 30)). Also, the guide collects emotional reactions experienced by the patient during the event (e.g., by pulldown). One or more emotions from the pulldown are added to create a list of experienced emotions. The list is automatically prioritized by ordering the highest on top. GUI prompts the guide on other significant events and data entry continues as described. When completed, the PC has stored multiple significant events each having multiple emotions entered. These emotions sometimes have shared or related symptoms; the correlations may be used in later steps.

f. In the GUI (not shown), the guide enters the patient's most desired symptoms to resolve (e.g., removing suicidal tendencies, better restful nights of sleep, or controlling outbursts of anger)(e.g., by pulldown). For example, these symptoms can be the checked boxes from data collected in item "c" above. By having this patient goal, the guide may manually select other entered events that may be associated with this goal. For example, the patient may want to resolve poor digestion, so the guide may focus upon emotions and events involving operations of the stomach such as eating and PTSD events which tend to stop digestive processes.

g. After data entry is complete, the PC may generate a report showing the patient's most frequently experienced/reported emotional responses (e.g., loneliness, fear, anger, frustration, etc.). The guide then chooses one or two of these emotions to filter/isolate significant events associated therewith (e.g., the events the patient has reported as having experienced such particular emotion(s) with). There may be an override by the PC 20 based upon a database and algorithms associating particular event types and particular emotional responses. For example, the database may show a correlation between a particular event type (e.g., suffering a near fatal injury) and a particular emotional response (e.g., guilt). If a given emotional response of the patient is deemed significant, the patient may have reported events the PC shows to be typically associated with such emotional response (but which emotion the patient did not report as being with the patient's experiencing that event). The PC may then add that event to the filtered events associated with the significant emotion.

The guide, by experience, may manually filter items (which may override automatic filtering) such as by using a check box (not shown). The guide may further enter additional selection criteria such as a maximum and minimum numeric significance value given to the past events (e.g., significance greater than 6 and less than 8). Various implementations may have different temporal orders of automated filtering and guide-controlled filtering.

These common events are used to make an instruction set. The instruction set will have the patient later re-live the filtered/selected events associated with the selected emotional theme(s) while experiencing temperature changes using the tub.

Depending upon the particular situation, there may be an initial concentration on a particular significant event and then the emotions associated with that event used to filter other events. For example, to create an instruction set, assume fictitious Jane wants to stop a self-cutting habit she may have had since breaking up with her third boyfriend. The guide or PC could select common emotional response themes that fictitious Jane exhibited around break-ups such as loneliness. The GUI (not shown) may enable the guide to individually flag (e.g., by check box), the emotion "loneliness" and the events sharing this emotion may be selected or otherwise isolated by the PC. Furthermore, the GUI (not shown) could allow the guide to filter these common events individually via check boxes and associate them to the instructions/desired goal. This instruction set could be sent to the RSI (e.g., in a realtime download or other data transfer) or they could be printed.

The results of the PC, guide and patient data collection and filtering of significant events becomes an instruction set for the patient to re-visit later. In one example, the instruction set contains commonly grouped (e.g., by emotional response, medical conditions, and/or the event type) past significant events in reverse chronologic order (e.g., with most recent event first). The instructions include a sequence of steps for the patient to re-enact or revisit later using the tub. Enough details from the data collection may be stored in the instructions for the RSI to guide the patient's re-visitation.

The next part of the process is a more direct interaction of the patient with the system hardware while operating independently (without the guide). FIG. 3 shows the activities the patient makes with the RSI 40. The RSI delivers the instructions from the PC. Instructions are delivered visually via the RSI's display and/or as audio commands via speakers.

The patient interacts with the RSI to complete the created instructions step by step. The RSI records the patient audibly during the significant temperature application. The RSI has temperature sensors to monitor and record the bath temperature and assist with the filling instructions (e.g., by audibly or visually indicating measured temperature and desired temperature or a difference or simply a binary increase or decrease instruction). For instance, if the incoming water was colder than the desired hot temperature (or the water heater temperature falls below a desired level), the RSI interrupts with an instruction for the patient to wait for the water heater to attain a hotter temperature and/or to slow down the input flow rate to achieve higher temperature.

Figure 17:
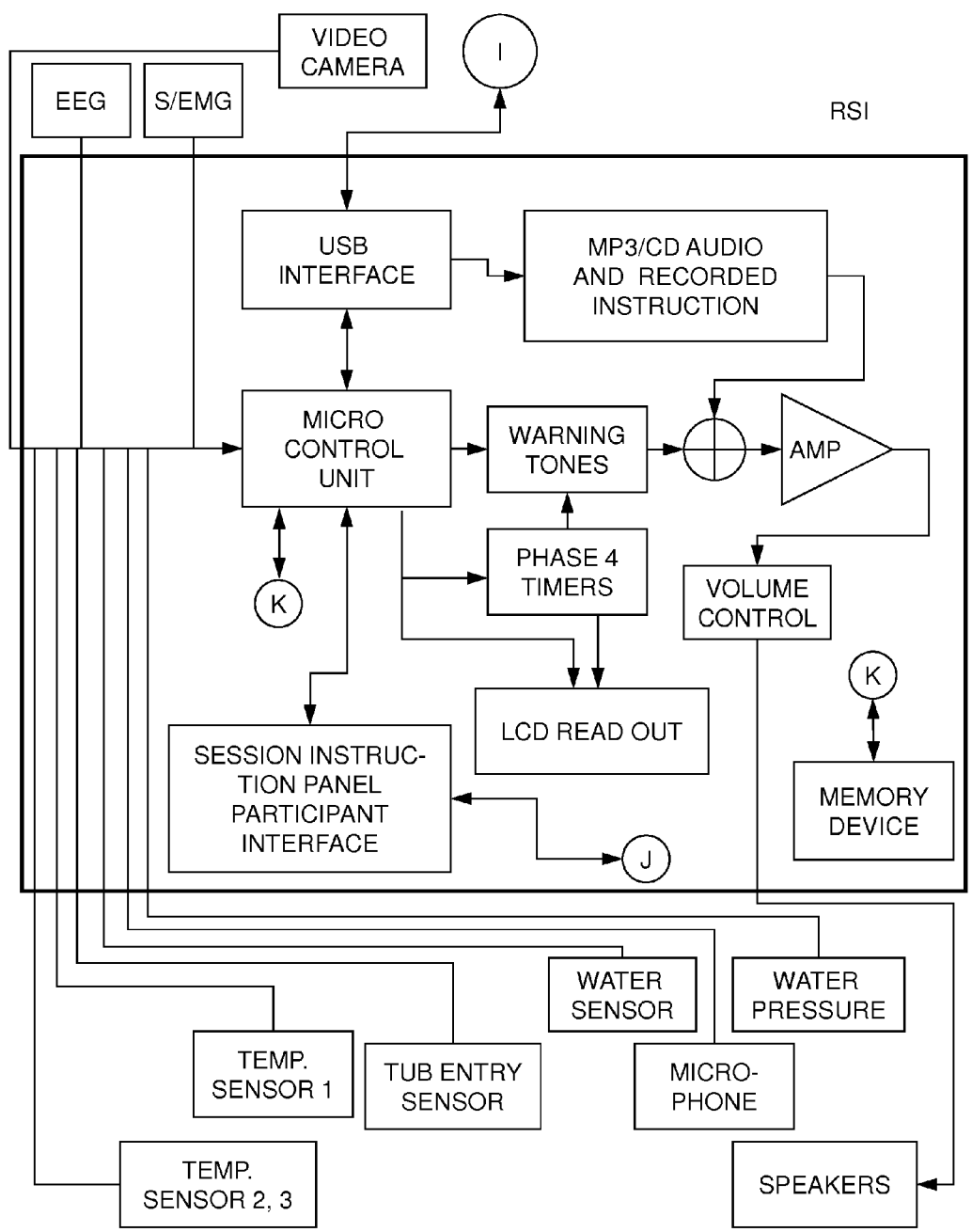
FIG. 17 is a schematic representation of remote system interface (RSI) subsystems.
Figure 19:
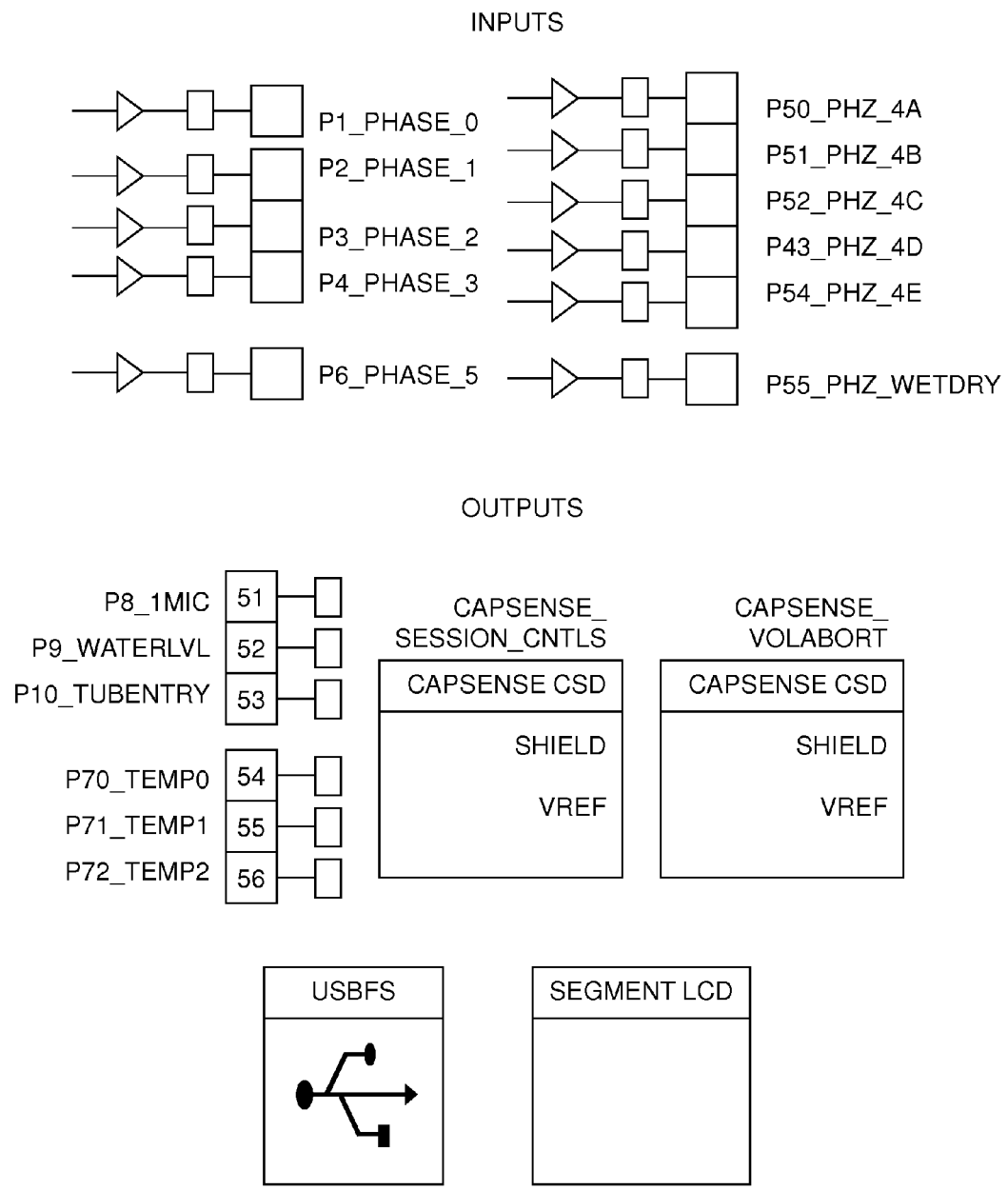
FIG. 19 is a schematic representation of a microcontroller unit architecture.
Figure 20:
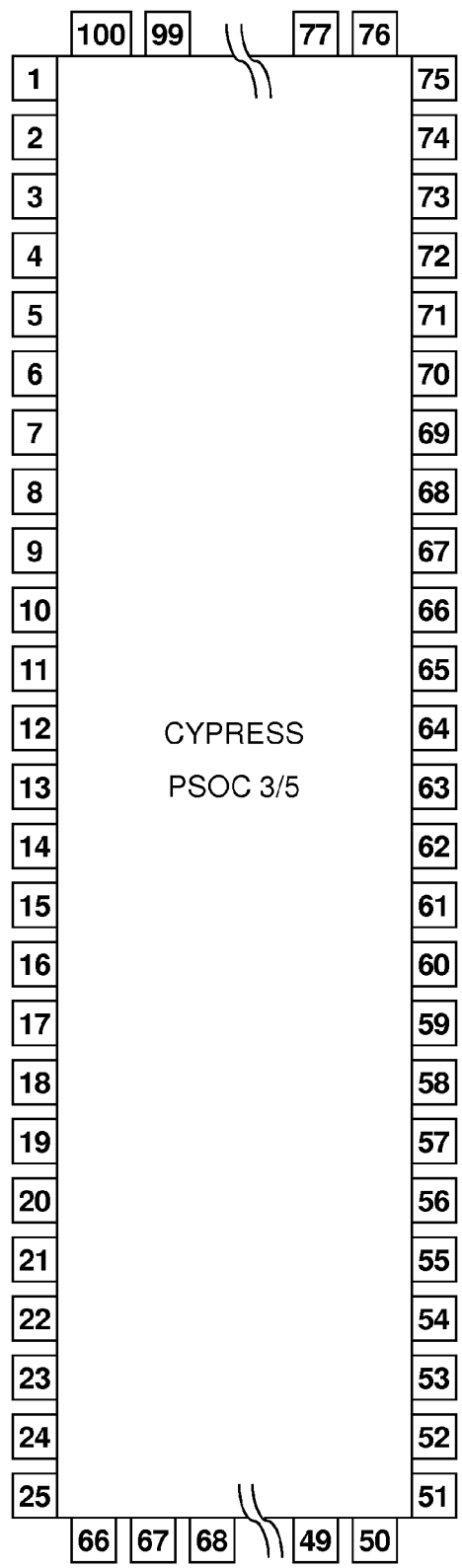
Figure 24:
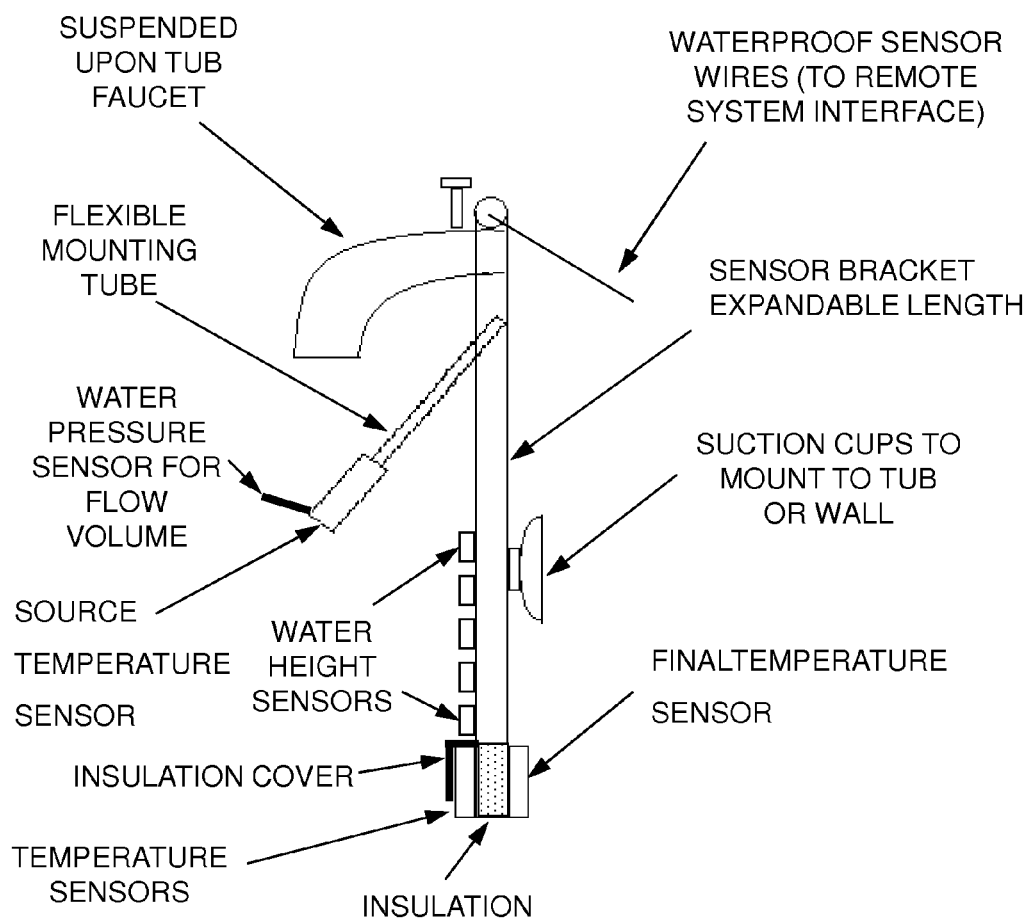
FIG. 24 is a partially schematic view of a sensor mounting bracket for a tub.

A layout of possible sensors (e.g., temperature, water pressure, and fill level) that the RSI could interact with for filling the tub and maintaining its instructed final temperature are shown in FIGS. 17, 19 and 24. The sensor data may be combined with tub characteristics and water heating system characteristics in the RSI's programming in order to create a tub fill sequence. For example, fill sequences use water level and flow sensors and timing signals to inform the patient how fast to fill a tub with hot water to achieve a desired temperature.

The RSI comprises a touchscreen 42 (FIGS. 18 and 42A) which may be on a tablet or wireless/cellular phone 44 (FIG. 43), and internal hardware and external connections (FIG. 17). The RSI can communicate recorded or synthesized voice (e.g., a series of audible instructions to re-live or recall specific events selected by the guide and/or the PC as discussed above), non-voice signals (alarms, etc.), and music with the patient via speakers.

Also, the RSI may communicate data from the patient's use of the tub and RSI. For example, data may be communicated back to the guide's PC 20 or any central or cloud system managing the process (e.g., in real time or delayed/discretely). This communicated data may include actual temperatures associated with each instructed re-lived experience. It may also include audio and/or video recordings of the patient's responses. It may also include patient inputs such as confirmations of completion of each step or activity or may communicate the lack of such patient input.

Figure 18:
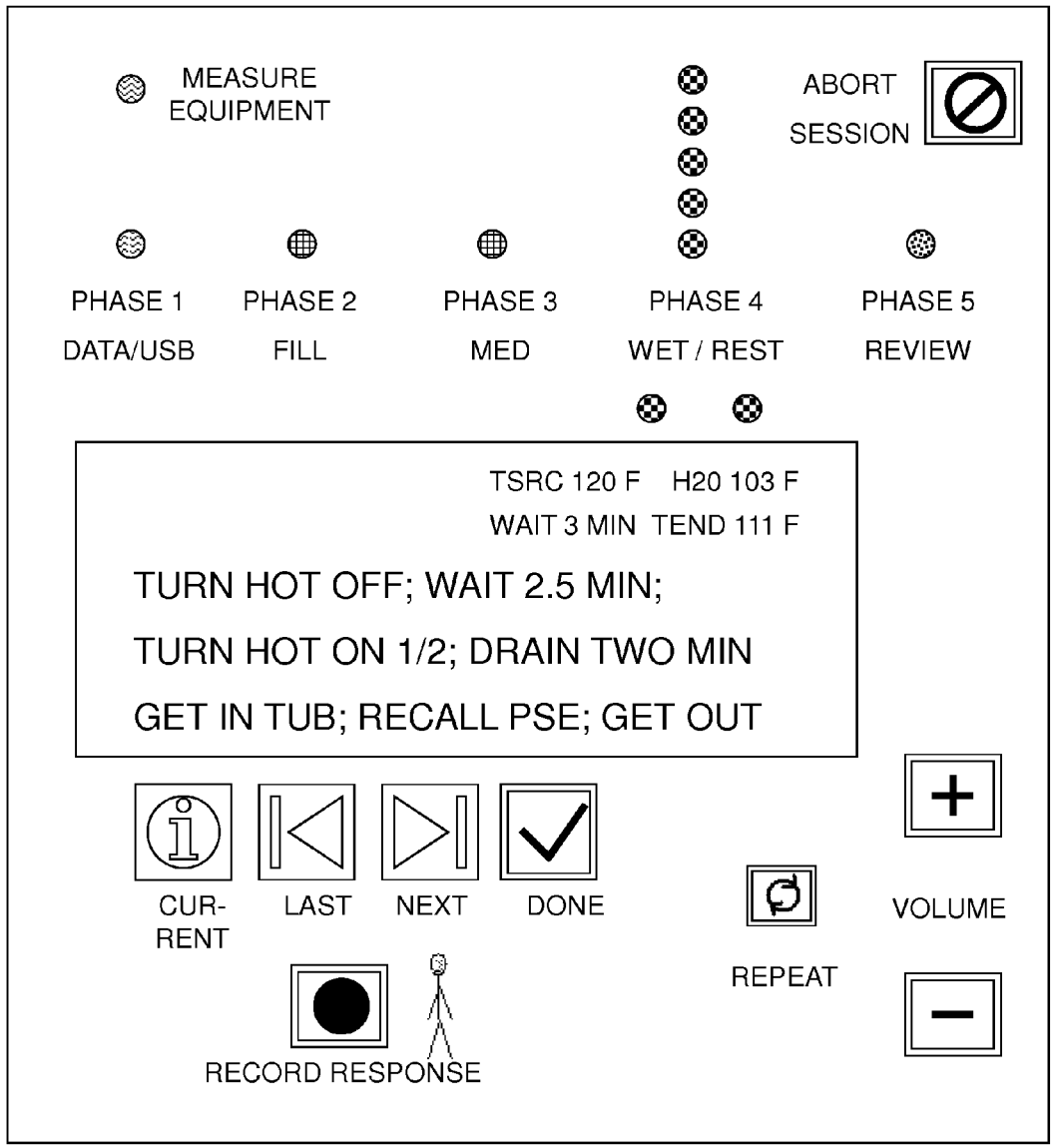
FIG. 18 is a schematic representation of the RSI patient panel interface.

Embodiment I Part 2 a. The RSI 40 (FIG. 3) directs/informs the patient as follows:
 1. to upload digital instructions previously created by the guide and/or PC and patient- or guide-selected meditation music (e.g., in real time and/or discretely unless previously uploaded by guide and PC);
 2. to fill the tub to the specified temperatures for each stage. A first use initialization may involve entry of tub characteristics, water heater characteristics, and the like (FIG. 25);
 3. when tub temperature is ready (e.g., via by alarm tone or display or voice);
 4. to test the recording capabilities for the RSI record response button of (FIG. 18);
 5. to follow each instruction given by the RSI, and to acknowledge the completion of each instruction through the RSI button "done" (FIG. 18);

b. The RSI leads the patient through the instruction set items directing patient through a series of actions to focus on each past significant event by mentally re-enacting the event. The RSI may direct the patient to notice any feelings and emotions surrounding the re-enactment and optionally record or enter information about same. The RSI may direct the patient to release a stuck emotion, magnify the emotional response, respond with appropriate tears or screams or other acts. The RSI may be programmed to record these body reactions for approximately 15 minutes while the patient is in the heated tub. The RSI may be programmed to abort the session if the body reactions become to emotionally intense (e.g., muscles cramping excessively or recollection of incest surfaces). The RSI receives input from the patient confirming completion of each step (e.g., each past event revisited emotionally);

c. The RSI delivers rest break direction outside of tub after an appropriate time lapse.

d. The patient finishes instruction set or ends session prematurely.

e. The patient meets with the guide for new instruction set(s) within 1 to 48 hours (FIG. 15).

Figure 13:
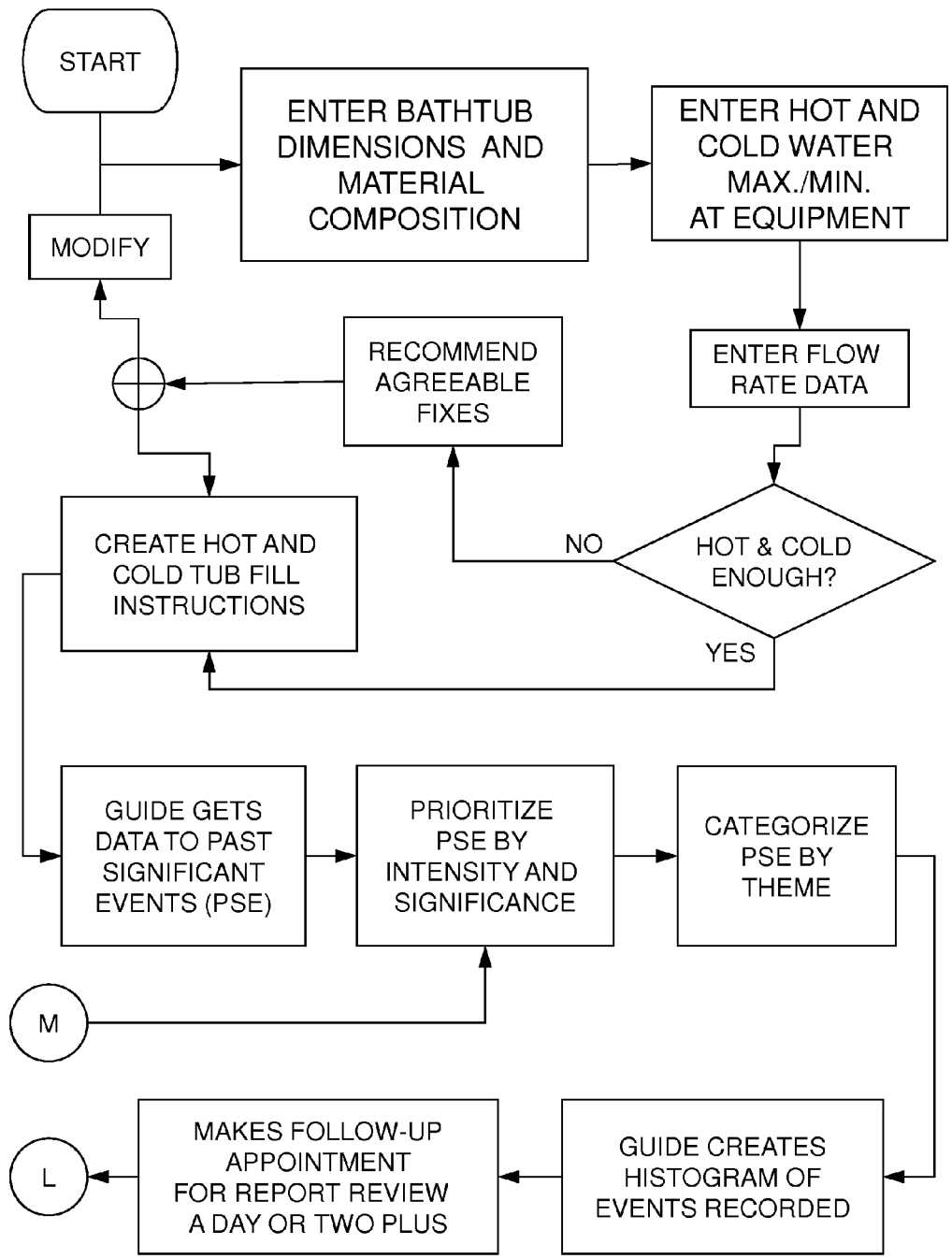
FIGS. 13 to 15 is a flowchart of steps taken by the guide with a personal computer (PC) and application interface that collects the patient's significant events.
Figure 14:
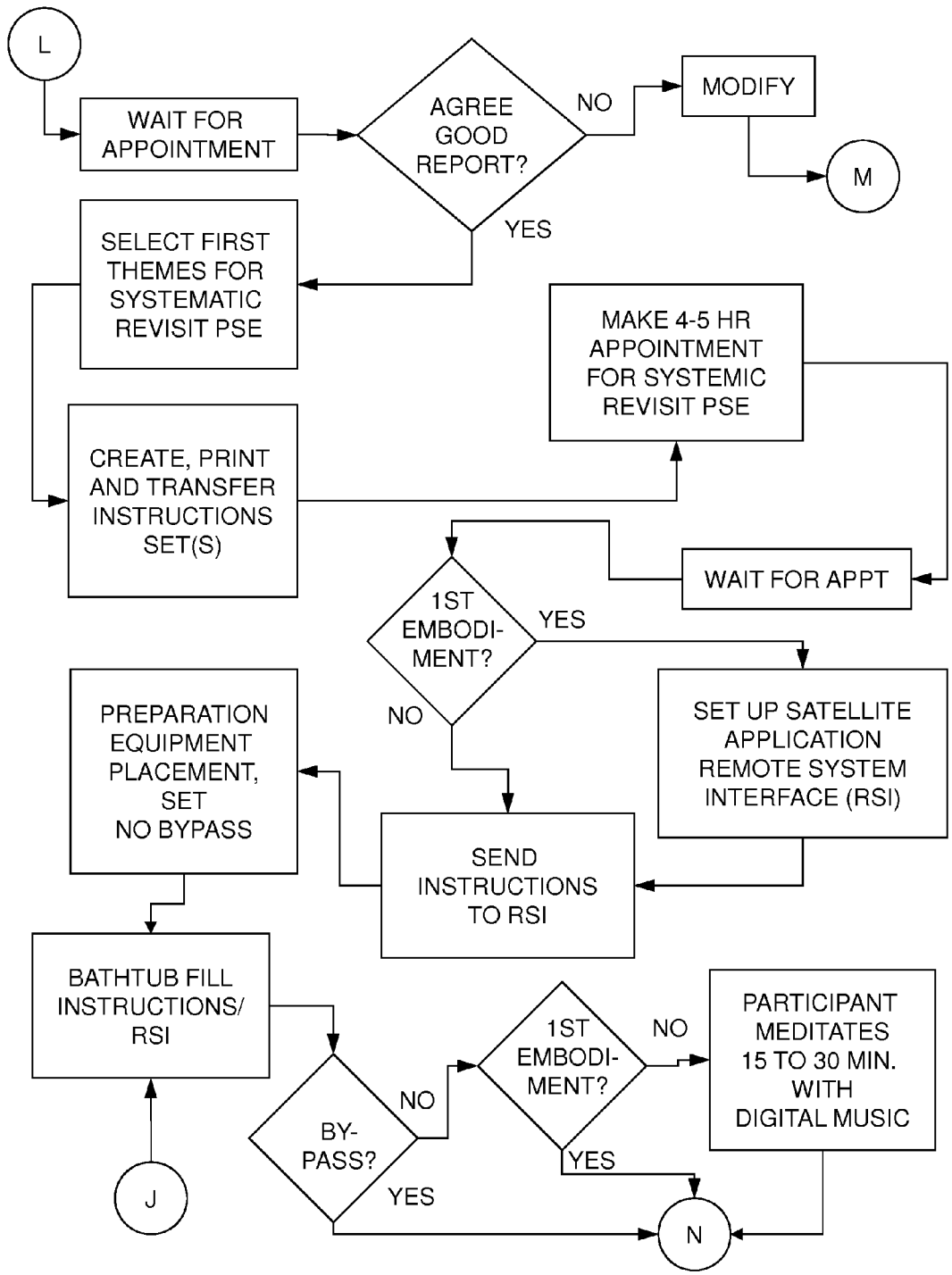
Figure 15:
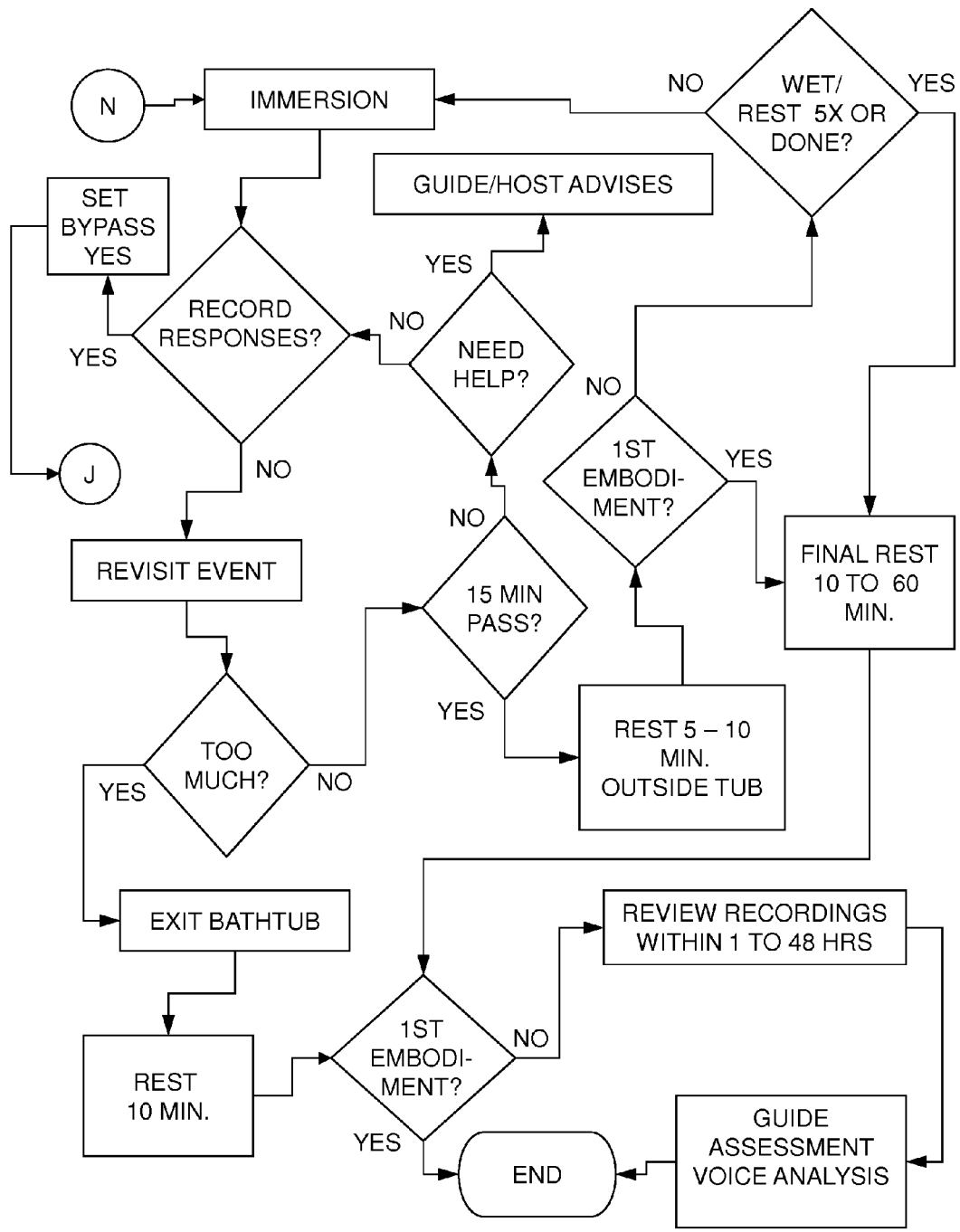

FIGS. 13 through 15 show application interface program steps. The application interface is or has a database application instruction set. The application may create a fill instruction sequence that has parameters for tub materials and maximum and minimum temperatures achieved by the tub system. Adjustments and remedies may be made to address insufficiencies of the tub heating or cooling system. For instance if the water minimum temperature is higher than the lowest desired temperature for a cold appendage bath, then ice could be recommended (by the PC, RSI or other hardware) as a remedy. Measuring the volume of appendage bath water would give an estimate of the amount of ice that would be needed to rectify cold water being too warm. Another solution would be to rent a hotel room that has a suitable heating system supplying a suitable tub in the event the patient had no tub available or insufficient heater characteristics.

Figure 31:
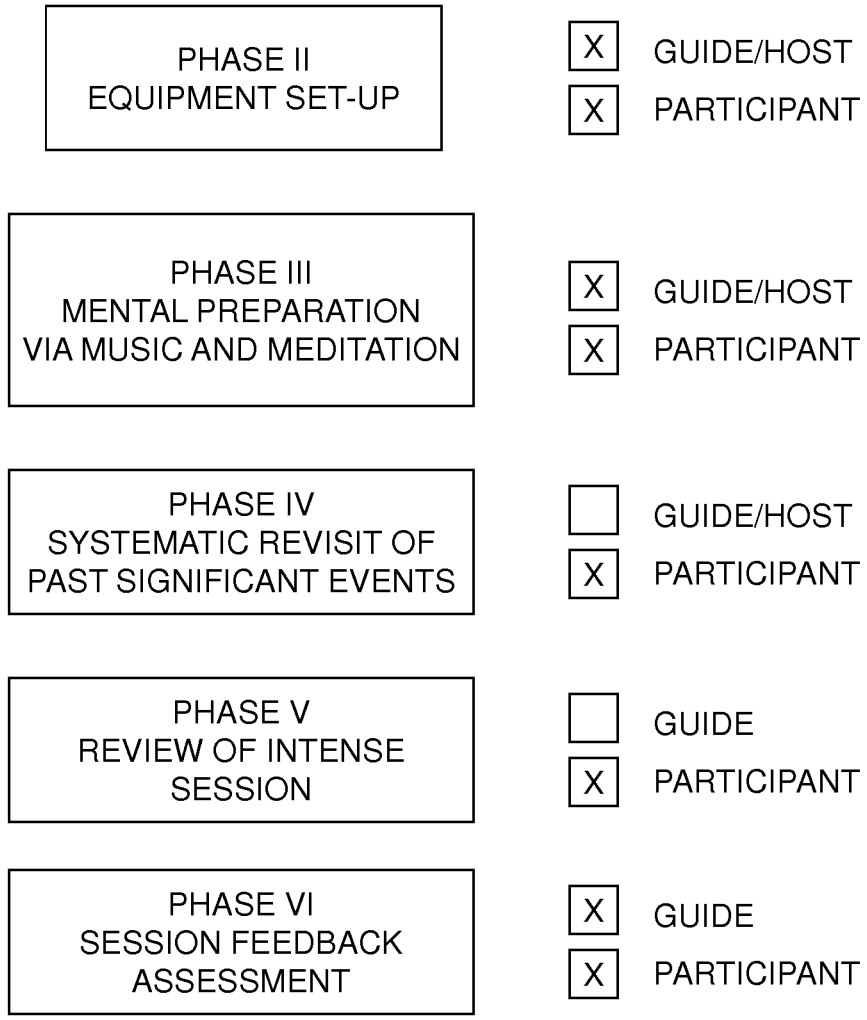
Figure 32:
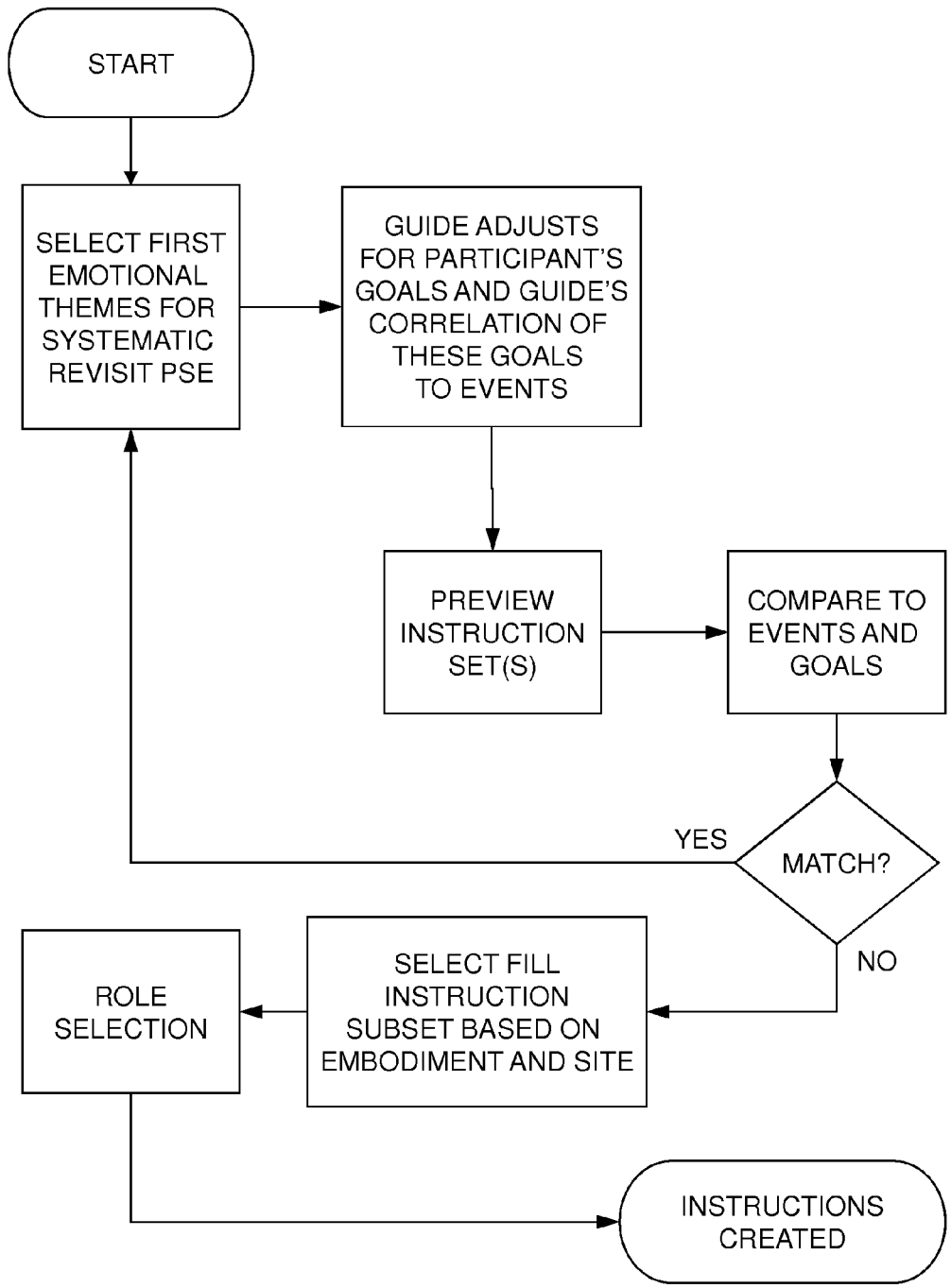
FIG. 32 is a flowchart of how the instruction set(s) are created.

FIGS. 25 through 30 show a sample database application interface with GUI for the guide's collection of data. Starting with the patient's personal ailments and continuing with immediate family members relationship data. Next medical histories of self and family are taken. Group 5, eligibility questions in FIG. 29 show anxiety symptom questions in various categories; each category may have several questions with yes/no responses and dates started and last occurrence dates. A form for entering the significant events is shown in FIG. 30. FIG. 31 shows the guide's selection of roles for the creation of instructions. The guide creates the instruction set as shown in FIG. 32. The instructions are printed out for the patient and made available for digital upload/transfer into the RSI. Instructions could contain illustrations (FIGS. 33 through 36) of expected positions to be assumed when experiencing heated water, especially for the first time. A small warning may be provided to get patient's head up slowly and in stages by kneeling, sitting and then standing as the blood vessels in the head dilate and could lead to fainting.

Figure 16:
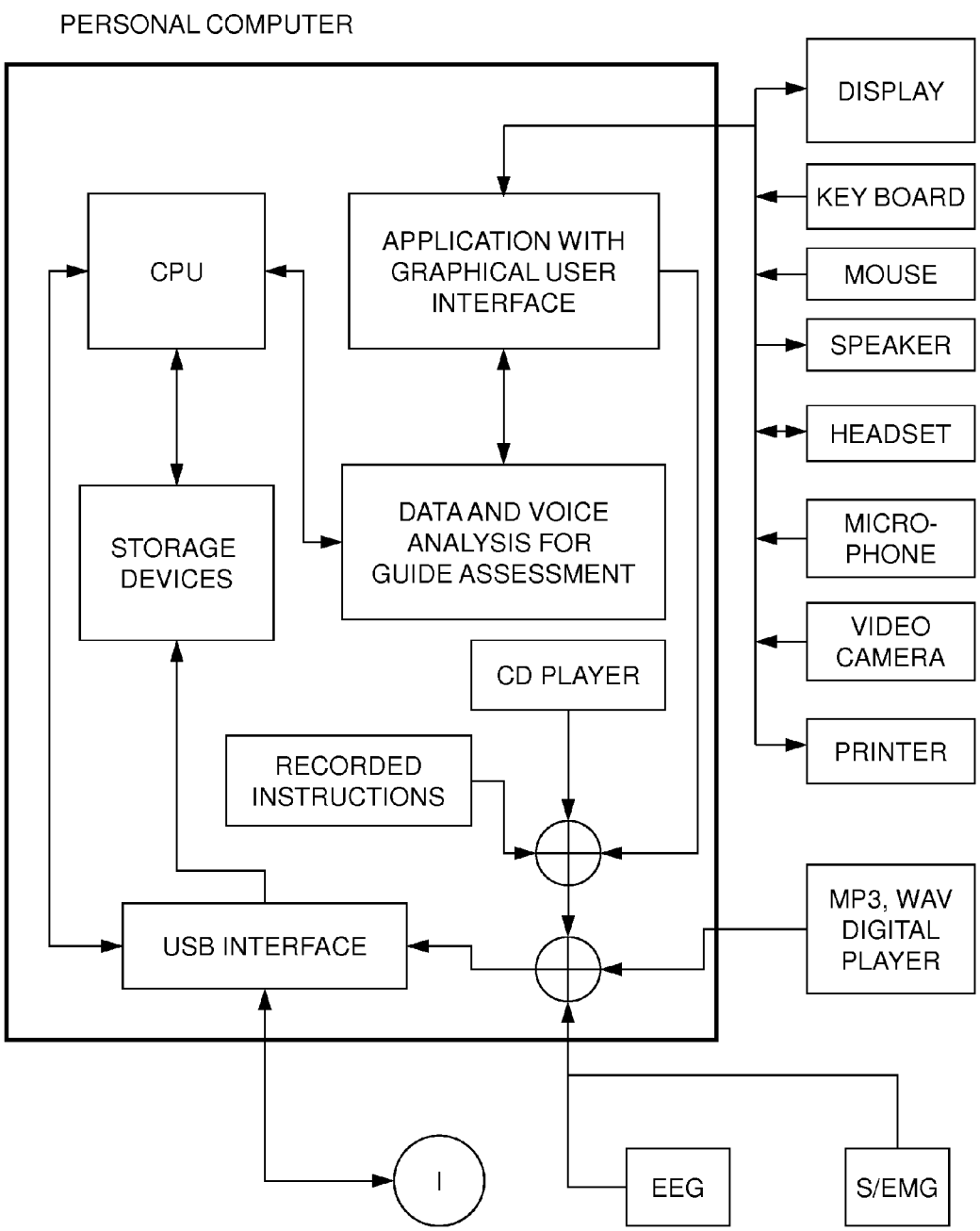
FIG. 16 is a schematic representation of the PC/application hardware interface.

FIG. 16 shows hardware subsystems of the PC 20. It links the application to the RSI through USB and through a session instruction panel/patient interface as these components are shown in FIGS. 17 and 18. The computer could receive input via standard devices (keyboard, mouse, microphone or headset) and output information to its appropriate devices as well (display, printer, speaker or headset). One or more storage devices may be used to store patient data collected by the guide and recorded session data uploaded from the patient's significant temperature change. A central processing unit may be used by the application interface and any data or voice analysis programs or routines. A method to play the patient's desired meditative background music could be through CD player, MP3, WAV or other digital medium and sent to the RSI via wireless or wired connection (e.g., USB). The USB interface may be available for uploading or saving of recordings initiated at the RSI. In this first embodiment, because the guide and patient will be at differing sites than in the other embodiments, a remote satellite application could be used to act like a hosting site's PC and satellite application at the patient's site for setup or for upload and download interactions. More details on these functions are discussed below in other embodiments. Alternative devices such as systems or sensors of type electroencephalography (EEG) or surface/electromyography (S/EMG) can be used as means for measuring data from the patient. These measurements could aid in measuring emotional brain wave signals and muscle responses of the patient respectively.

Figure 33:
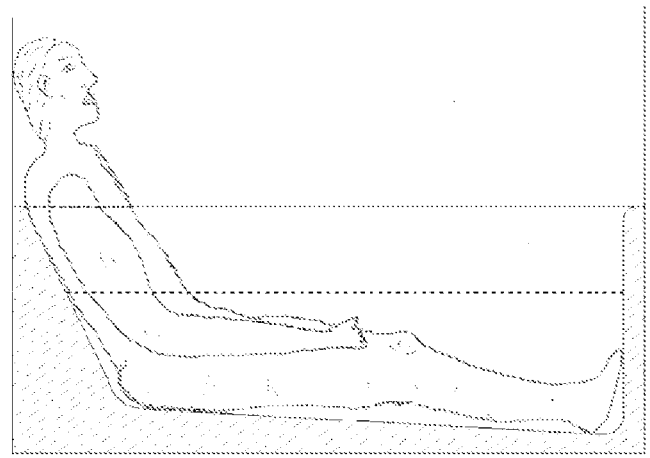
FIGS. 33 to 36 are views of a series of positions of the patient using the tub.
Figure 34:
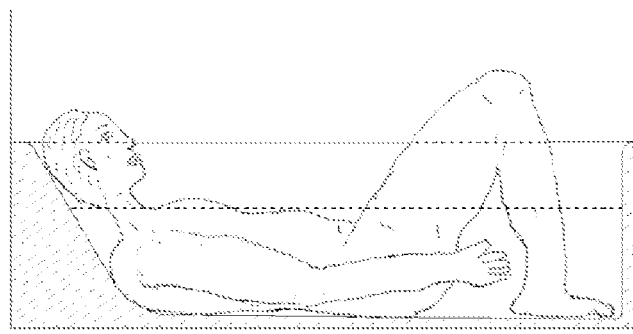
Figure 35:
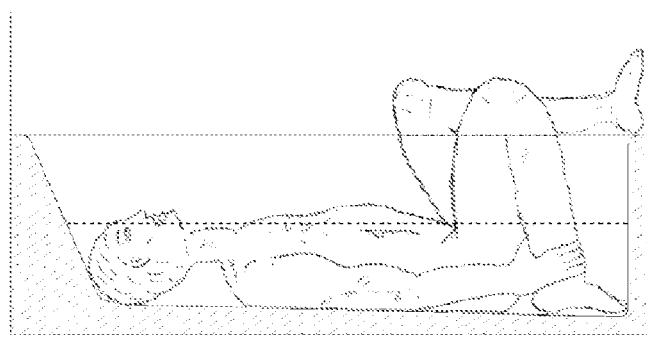
Figure 36:
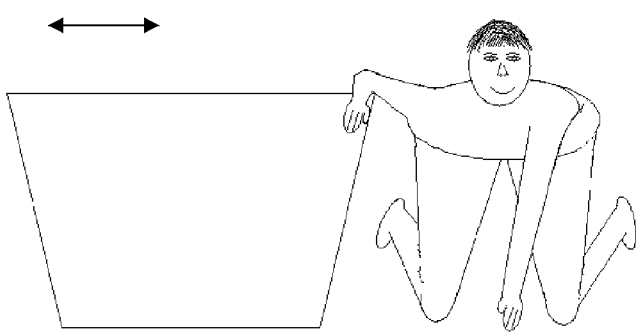
Figure 38:
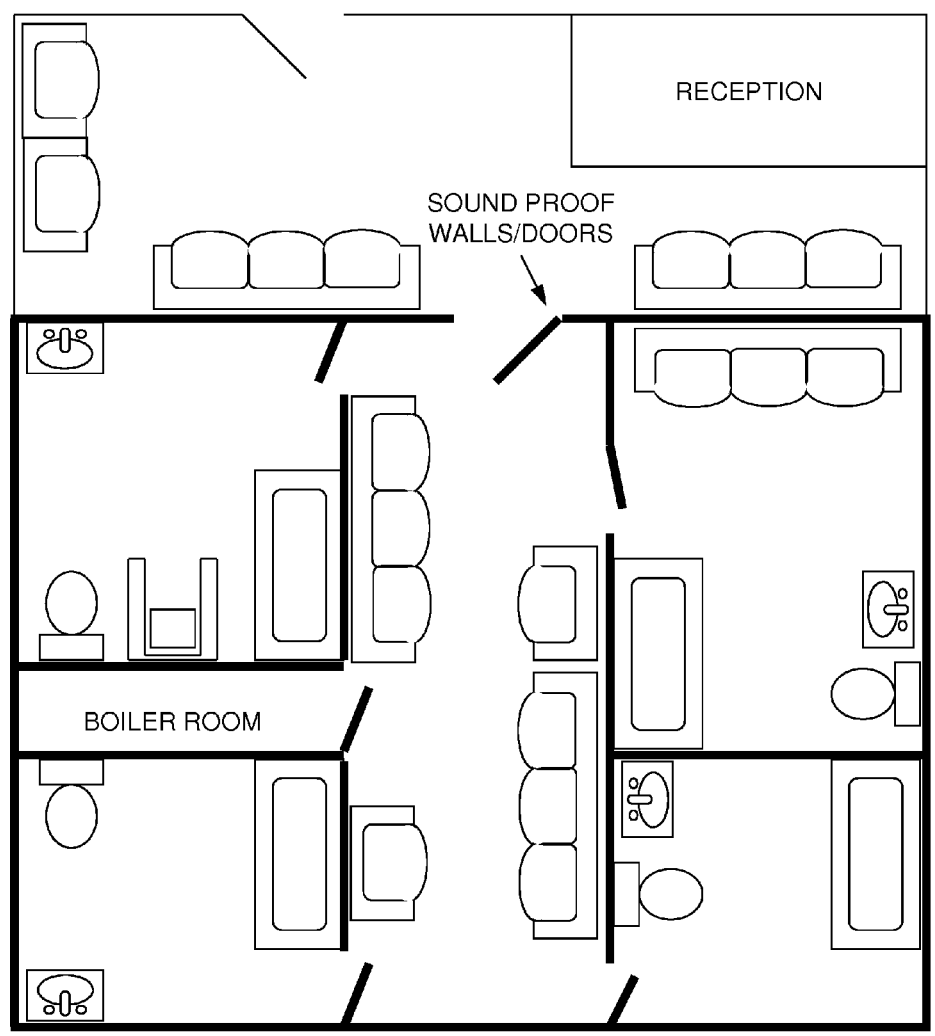
FIGS. 38 and 39 are a plan for a hosting site with recirculation units to maintain temperature per instruction sets provided.
Figure 39:
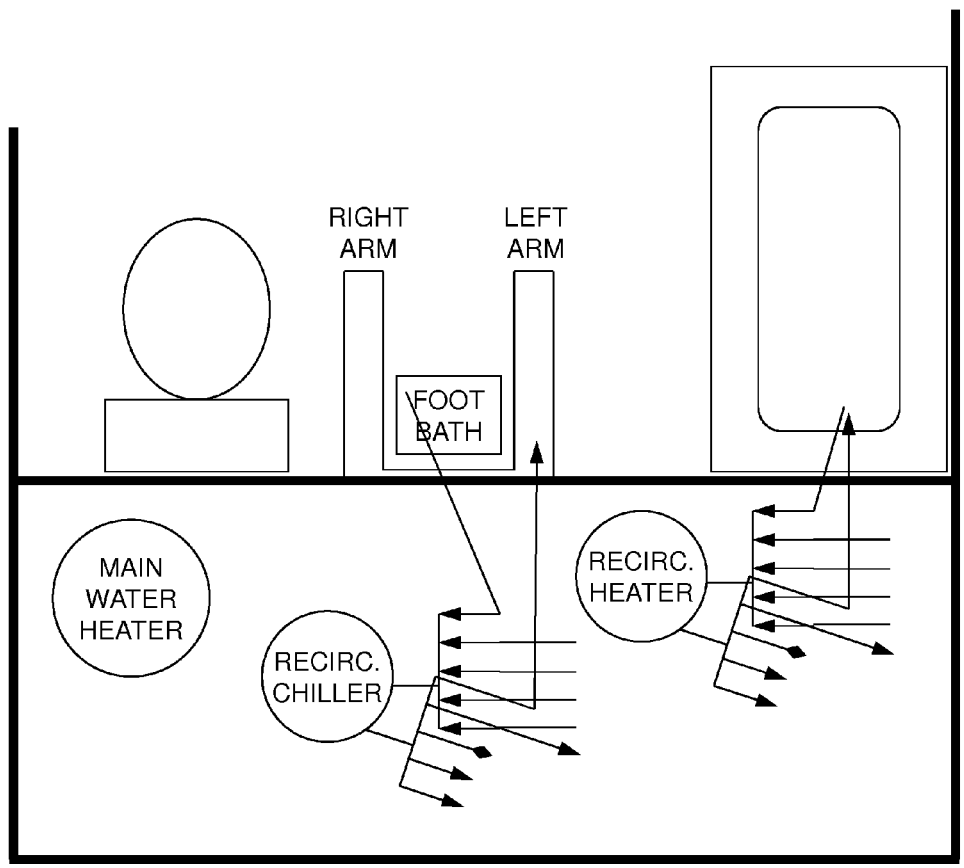
Figure 40B:
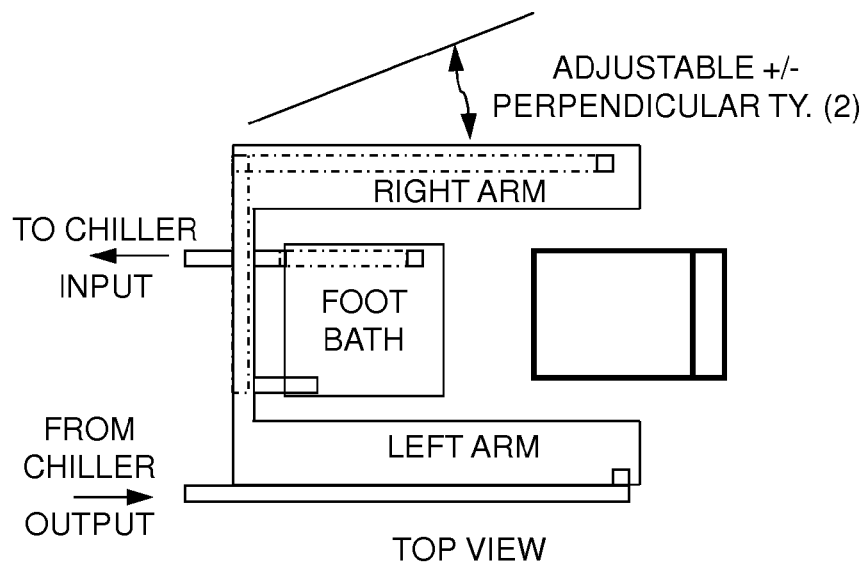
FIGS. 40A and 40B are side and top views of an appendage bath assembly.
Figure 40A:
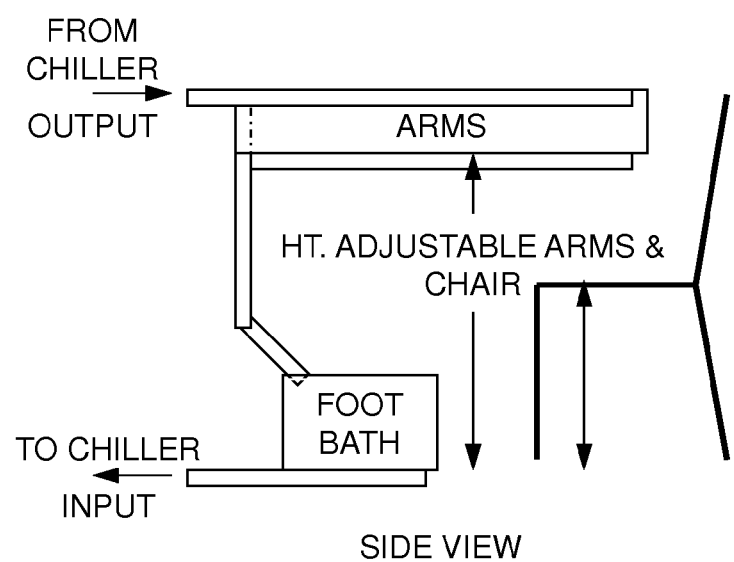
Figure 41:
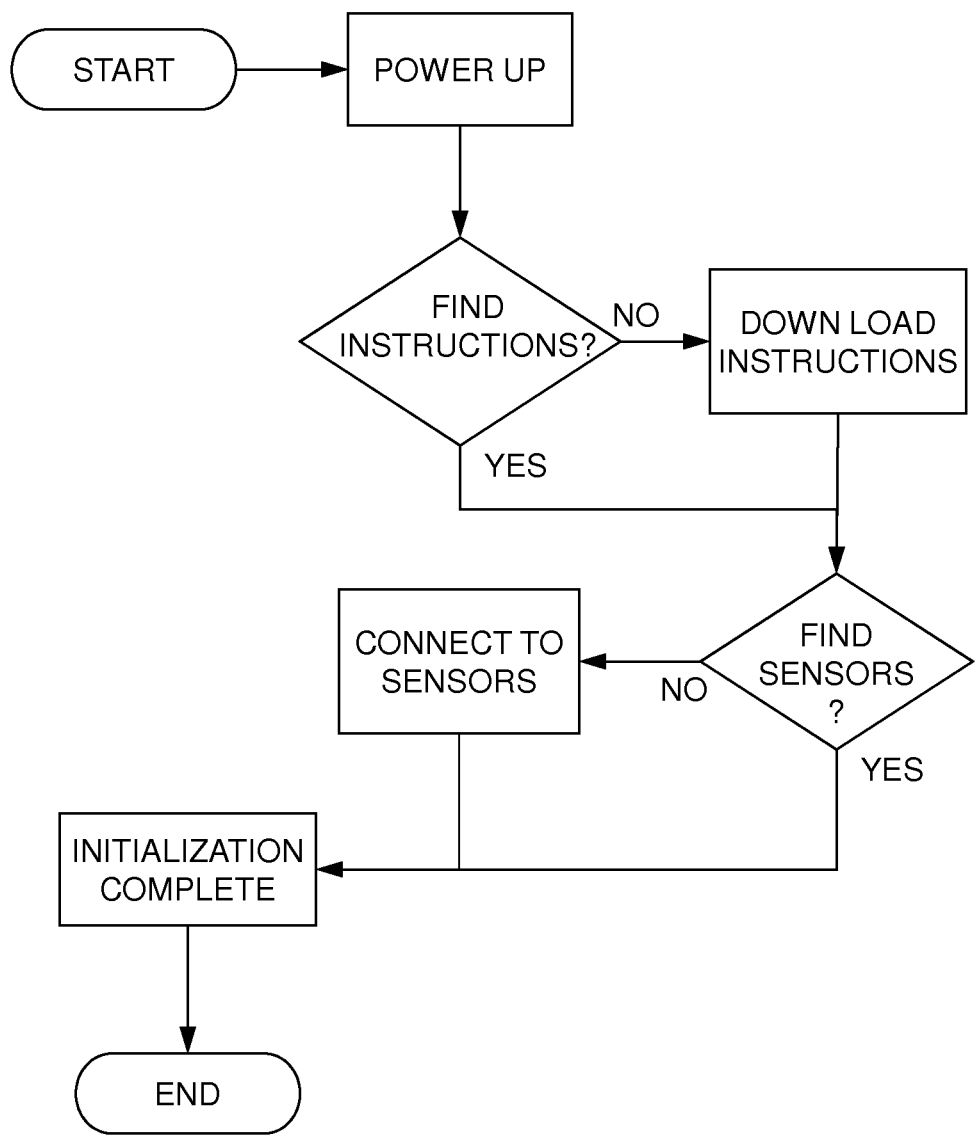
FIG. 41 is a flowchart of the initialization of the RSI.
Figure 42B:
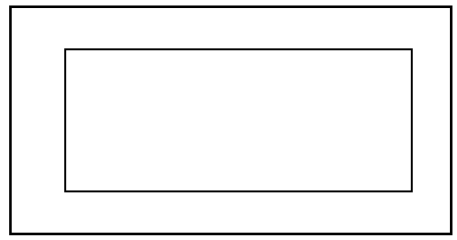
FIGS. 42A, 42B, and 42C are front top and side views of a first RSI enclosure.
Figure 42A:
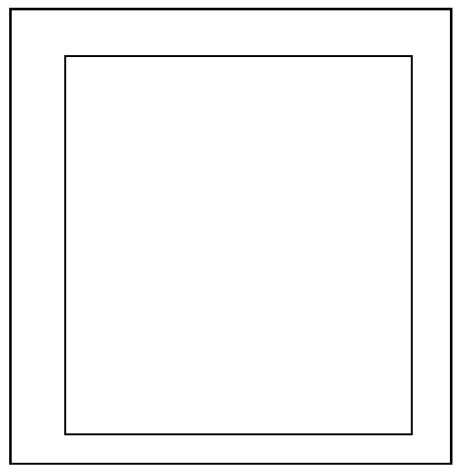
Figure 42C:
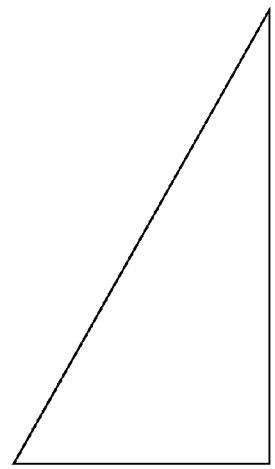
Figure 43:
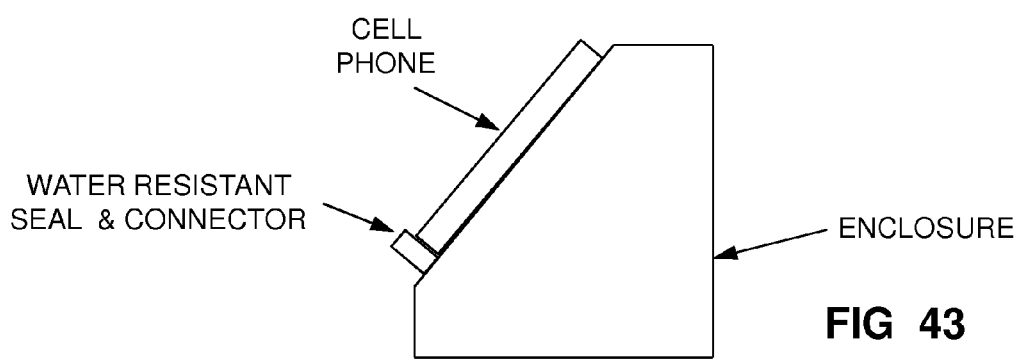
FIG. 43 is a side view of a second RSI enclosure.

FIG. 33 shows initialization logic; it shows the power-up logic and connections to the sensors and instructions. FIGS. 17 through 24, 42 and 43 show various RSI hardware. FIG. 18 shows a layout of the functions and sample instructions that could be displayed to the patient. Also shown are the button functions and possible display lights to indicate the progress of the instructions or the mode of the RSI. One mode is the "Equipment Measure" mode where the patient's heating and cooling systems are measured by the RSI. FIG. 18 shows an embodiment of Cypress Semiconductor's programmable system on chip version 3/5 component layout. Other microcontrollers could be used. It shows the LED outputs as shown for the interface panel, Input signals from two capsense devices one for volume and the other for the instruction buttons of "Current", "Last", "Next", "Done", "Abort", "Repeat" and "Record Response". In FIG. 18 they are displayed as separate buttons, but the capsense allows for multi-touch meaning that can be programmed by one versed in the use of the art of capsense and microcontrollers. For instance sweep of finger can be defined as next and the opposite direction as last. Two finger touches could also have meaning such as repeat. Furthermore, FIG. 19 shows the USBFS interface required for wireless audio transmission, interfacing with the application interface and the LCD segment driver to drive the display of instructions. FIG. 20 through 23 show the pin layout of the microcontroller. The clock signals to make the shown items operational are in FIG. 23. Two embodiments of an RSI enclosure are shown in FIGS. 42 and 43. An enclosure may be used to enclose the parts and connect to the sensors and possible USB cable for uploading purposes. Other embodiments are possible for the enclosure.

Operation

FIG. 2 shows the guide gathering information from the patient by using the application interface. As shown in FIGS. 25 through 30 the application interface has a series of entry forms for inputting similar data. The entry of data in the fourth enumerated item in FIG. 26 is made by body category in appropriate checked boxes. These text-boxes, in FIG. 27, load body-specific ailments as shown in FIG. 28 for the head. Other aliments will be loaded for the appropriate body zones selected. The data entry form shown in FIG. 26 enumerated as item 5 is further detailed in FIG. 29 has sample questions listed alphabetically in FIGS. 44A-44C. Item enumerated as 6 in FIG. 26 has a detailed data entry form as shown in FIG. 30 with the following questions listed alphabetically in FIGS. 45A-45C.

Figure 25:

In the case of the significant events, the guide has a method to evaluate the significance a using slider, the black vertical arrow pointing downward, that has descriptive words and a number related to its final resting position as highlighted in FIG. 30. This allows the application to prioritize events easily. FIGS. 31 and 32 show how the guide: selects a set of themes; correlates them to patient's goals; adjusts as necessary: selects roles per phase/stage and creates the instruction sets. The instruction sets are printed and uploaded to the RSI. Also, FIG. 25 shows tub parameters that can be collected to make initial instruction sets in conjunction with the application interface or recommend solutions when the hot or cold water systems are not able to reach desired end temperatures.

The patient then at appointed time initializes the RSI and follows the instruction set as prompted by the RSI. The RSI using the input sensors could be used to alter the initial filling instructions to ensure the tub is filled to the proper end temperature. The RSI could give a tone when the water is at desired temperature. The patient may be directed to fill the tub to appropriate temperature then to immerse him or herself in the tub assuming positions outlined in FIGS. 33 to 35 to expose the most area of their body. During immersion, the RSI will record the audio responses of the patient as they recall their past significant events. While contemplating details of their past significant events the patient will experience effects of a momentary stressful nature: pulse quickens; blood vessels dilate; respiration, sensitivity and alertness increase; muscles tense; emotions and anxiety surface.

Patients may be instructed to describe their body sensations and express feelings with screams, moans and tears. Yelling at imagined persons, that were involved in the patient's past significant events as if they were present, may also be instructed. While describing body sensations, the patient is well suited to describe the quality of the feeling and tagging it for several seconds by pressing record response button on the RSI (FIG. 18). Examples would be a muscle cramping or having spasms, numbness in a particular region or noticing an emotion surfacing. After immersion of a short period (e.g., approximately 15 minutes (e.g., 2-20 minutes) the RSI) would prompt the patient to rest upon the floor with towels above and below their body for 5-10 minutes then for a final rest of 10-60 minutes more in a comfortable reclining chair, bed or couch. The patient could complete unfinished instructions at another time. Once the instruction set is exhausted they would meet the guide again for another instruction set.

Description and Operation of Alternative Embodiments

Figure 4:
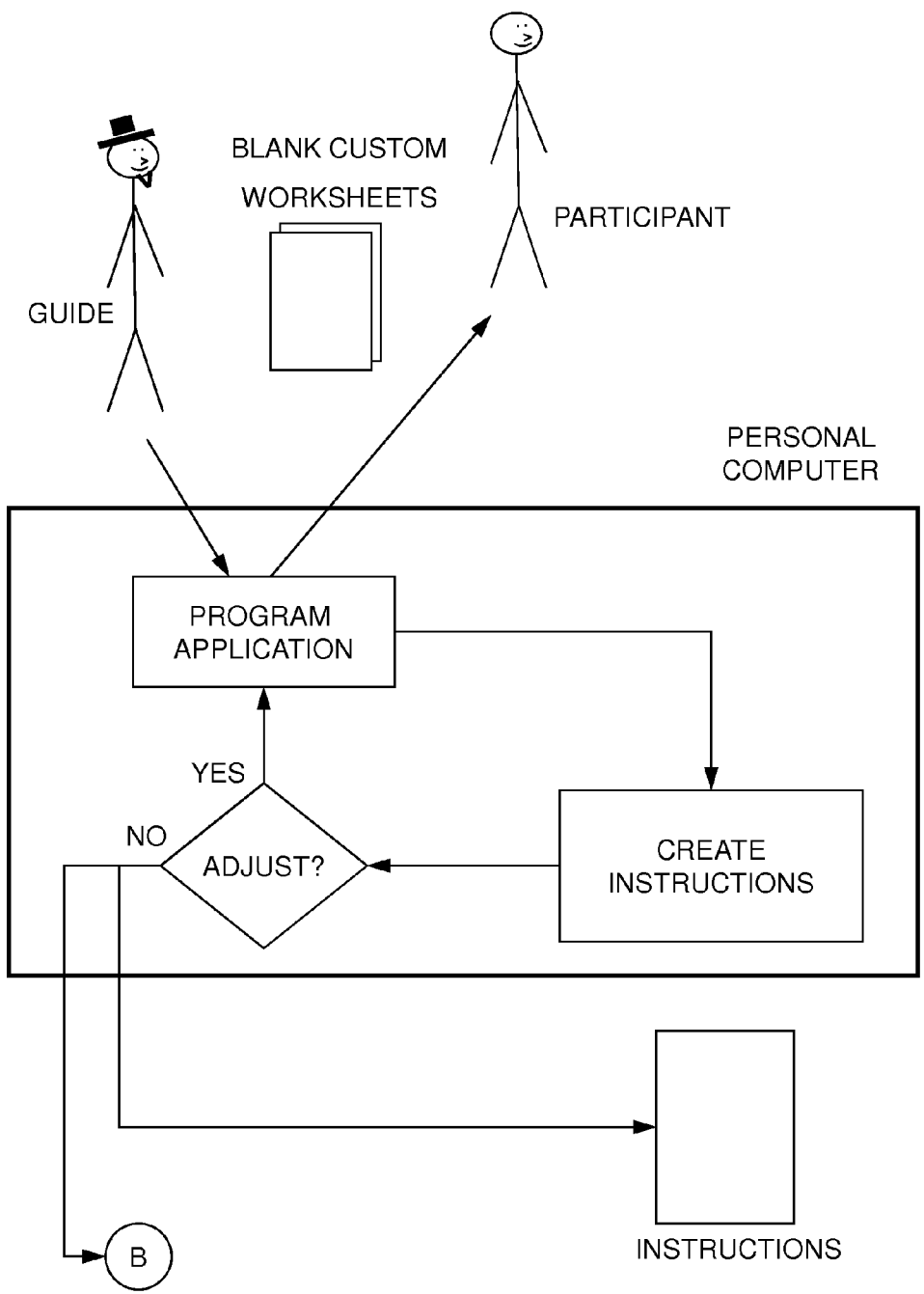
FIGS. 4 to 6 are a flowchart of a second embodiment adding a host role.
Figure 5:
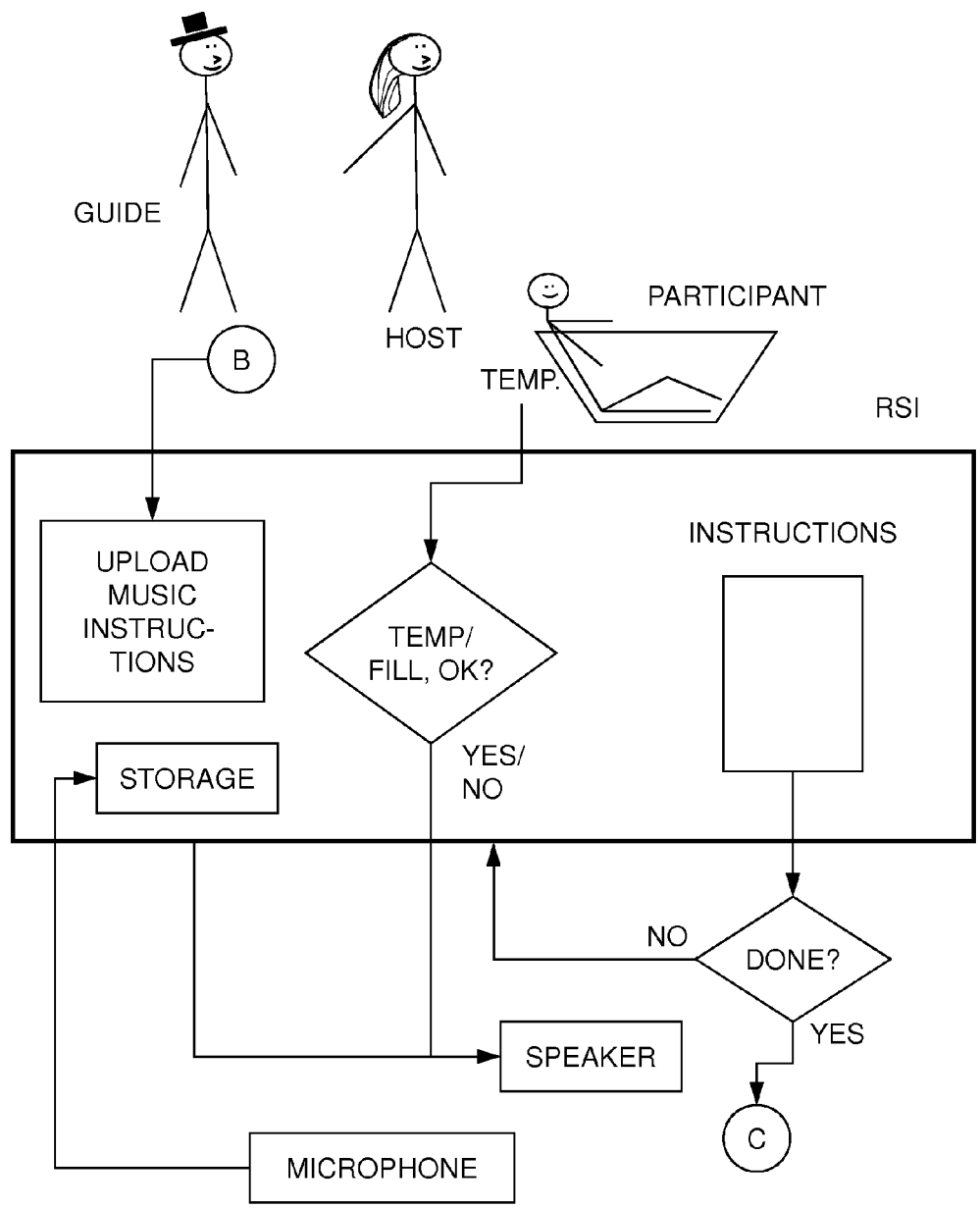
Figure 6:
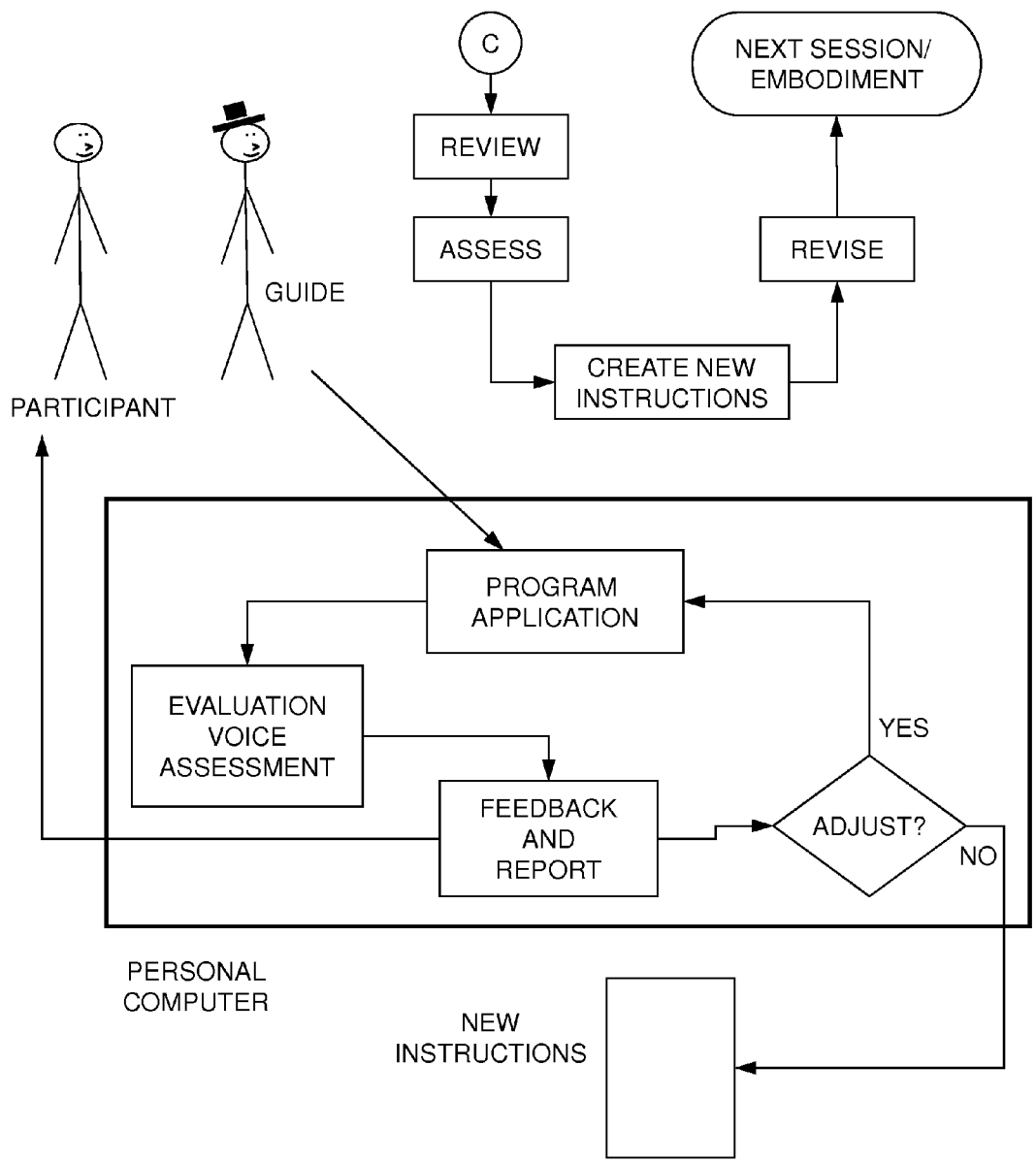

FIGS. 4 through 6 show a second embodiment. It uses the same devices as the first embodiment but in different ways. A "host" role is added to those of guide and patient. The following outline shows the steps taken for the second embodiment:

Embodiment II Part 1

In an exemplary sequence: Guide asks a patient for date of birth and prints a customized, blank worksheet; patient fills out worksheet; guide receives and enters past significant events and memories into application; guide asks for significance of events with slider and descriptors (FIG. 29); guide asks for most desired symptoms to resolve as a priority; guide receives the relative temperature and season that the events had occurred; guide selects a program criterion to select most likely common themes to remedy symptoms; program application outputs instruction sets based upon temperature, presenting symptoms and themes; guide adjusts scope of instruction sets by slightly enlarging scope or adjusting parameters of the program instructions-creating-algorithm parameters; guide records patient saying brief event descriptors for audio instructions and voice analysis.

Embodiment II Part 2

In an exemplary sequence: host and guide are present and available for the patient; host manages the facilities; host uploads digital instructions and music; plays meditation music; host fills tub to temperature specification; host signals when tub is ready; guide manages the progress and data collection of patient activities in conjunction with the RSI (tests recording capabilities (voice, tags); loads first instruction for patient; explains the control panel to get next instruction, skip, end request or call for help); RSI enables patient to summon the host and guide; RSI leads patient through instruction set(s) individual items; RSI receives input from Patient on completion of each item instructed; RSI delivers next instruction; RSI delivers rest break direction at appropriate time lapse; RSI instructs host or recirculation controls to maintain temperature during rest; RSI prompts patient to continue after rest; RSI prompts host for patients final rest.

Embodiment II Part 3

In an exemplary sequence: guide and patient review the recordings within 32 hours; guide receives hosted session data; program application verifies instruction integrity with temperature and patient responses; Voice analysis of patient recordings before, during and after hosted session; feedback reported by guide with or without the programmed assessments; new sessions instructions are created any new data of historic events added or priorities adjusted as necessary.

As shown in FIG. 4, the first difference in Embodiment II is that a blank set of custom worksheets are used for data about the patient life events. The following is exemplary instructions for making the custom work sheets. Start with a blank sheet of paper and make five columns. The first column has four rows with the headings: memories; favored persons; activities; feelings. The remaining four column have headings dividing the age of patient into equal or nearly equal time spans. Create a second sheet as above with the first column row headings: strong memories; emotional milestones; family attitudes; other.

The guide uses the filled out worksheets to enter the data. Proceeding as with the first embodiment until data is entered and instructions are made. FIG. 46 shows the instruction set created from a fictitious Jane's data selected and prioritized by the guide.

The guide audibly records brief descriptions from the patient regarding his or her significant events. These will be used as audio instructions from the RSI and for voice analysis as the before session reference.

FIG. 5 shows another difference. A host at a hosting site is accompanied by the guide. The host is witness for guide and patient interactions, for ethical reasons, and facilitates the setup of the RSI as well as carrying out the fill instructions to achieve final temperature in the tub and/or an appendage bath. The guide will assure testing of the RSI for capturing recordings as well as setting up the first instruction. The guide will explain the interface to the patient. A call for help can be issued. The RSI will carry out same functions as in the first embodiment directing the patient. Also the RSI will allow the use of multiple exposures to the significant temperature change and rest periods. Each new temperature exposure, the patient instructions pick up where the last exposure instructions had finished. A final rest of 10 to 50 minutes on comfortable furniture is again offered.

FIG. 6 shows the additional review and assessment of the session performed by both the guide and patient within 32 hours (actions not in the first embodiment). Data from the session is voice analyzed by the RSI. The voice analysis before, during and after the session are made by the program and guide and given to the patient. The program verifies the temperature was at desired temperature throughout the temperature exposure sessions. The guide creates a new instruction set for the patient.

Figure 7:
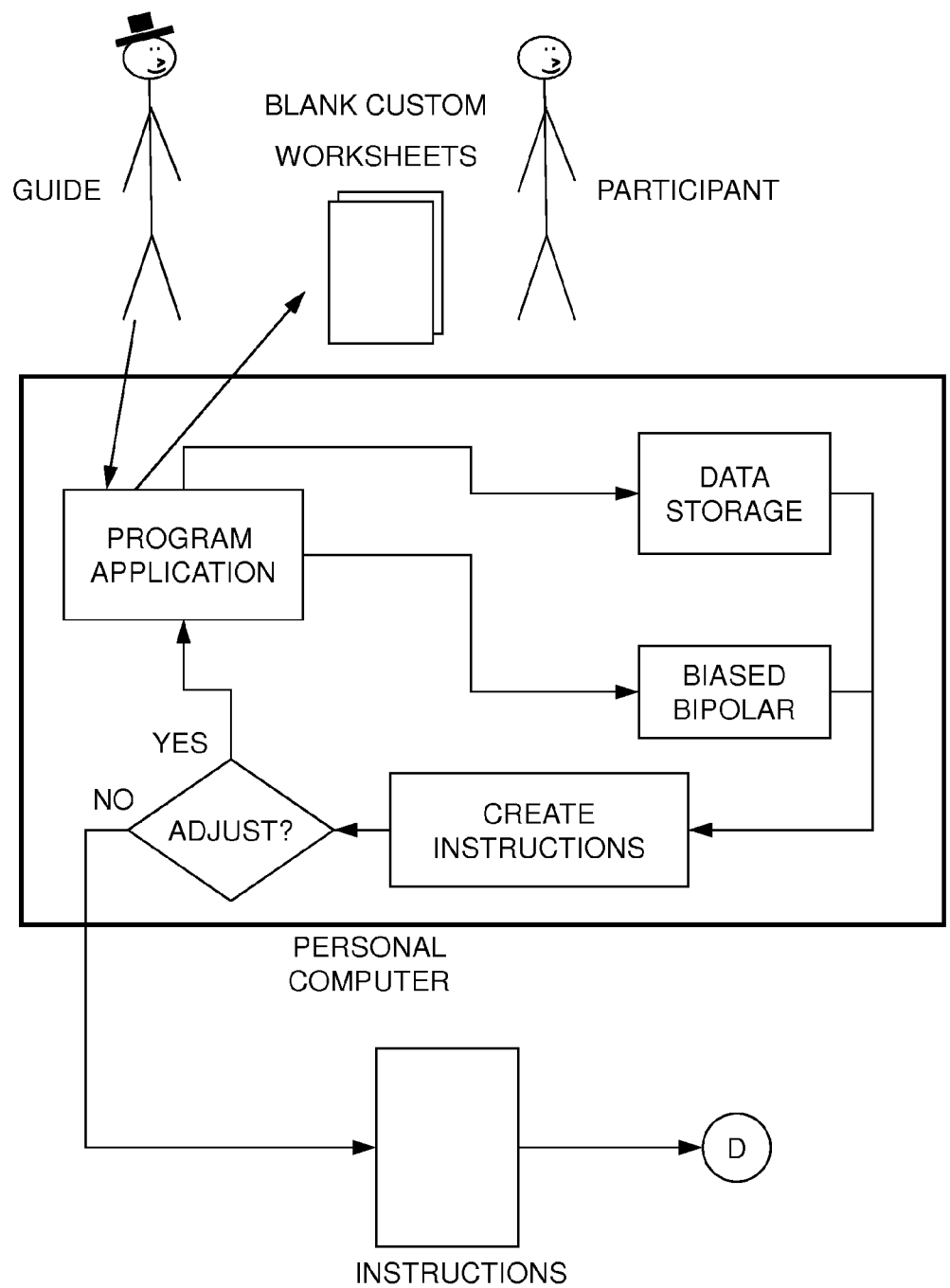
FIGS. 7 to 9 are a flowchart of a third embodiment where the guide is eliminated from some duties.
Figure 8:
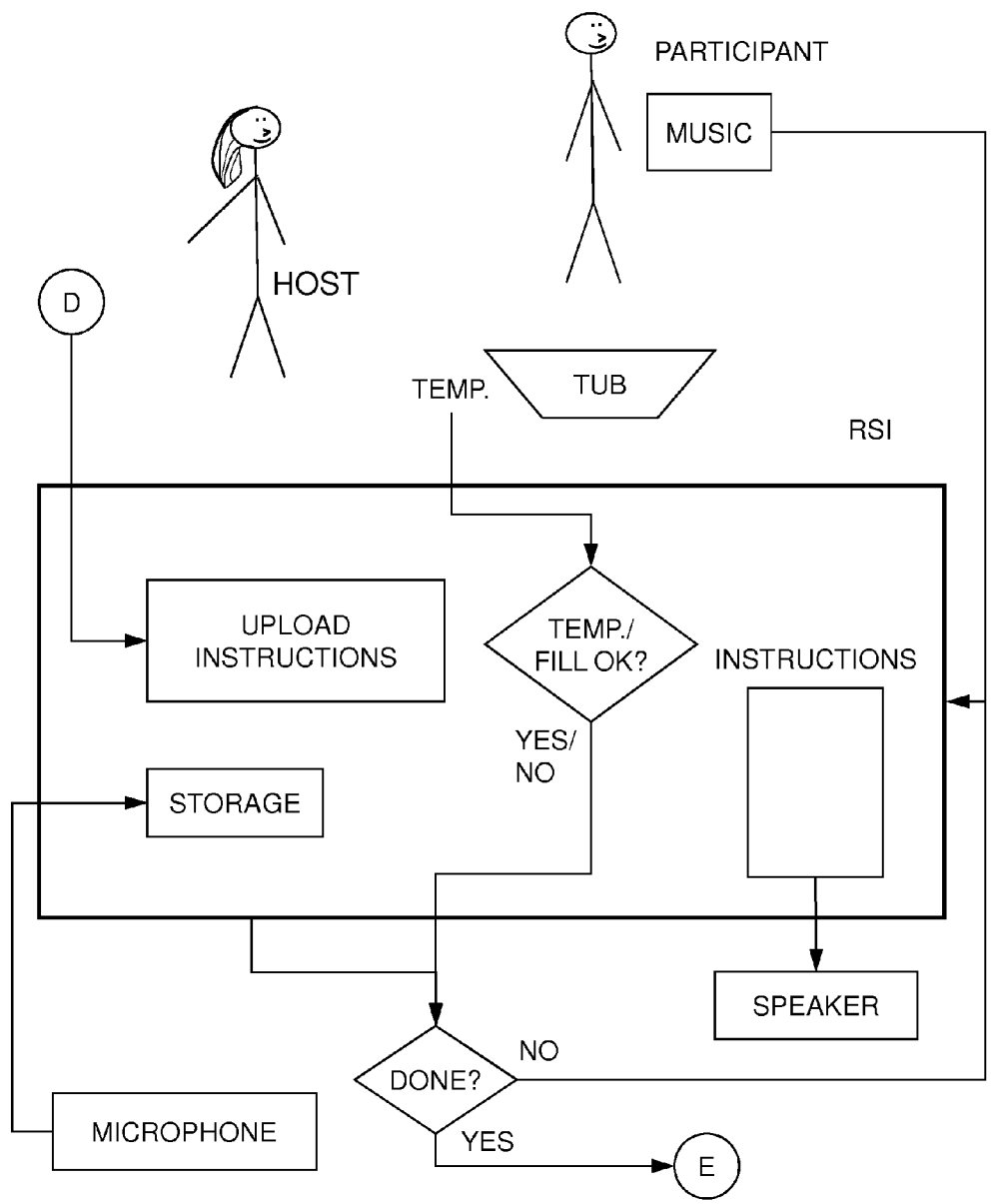
Figure 9:
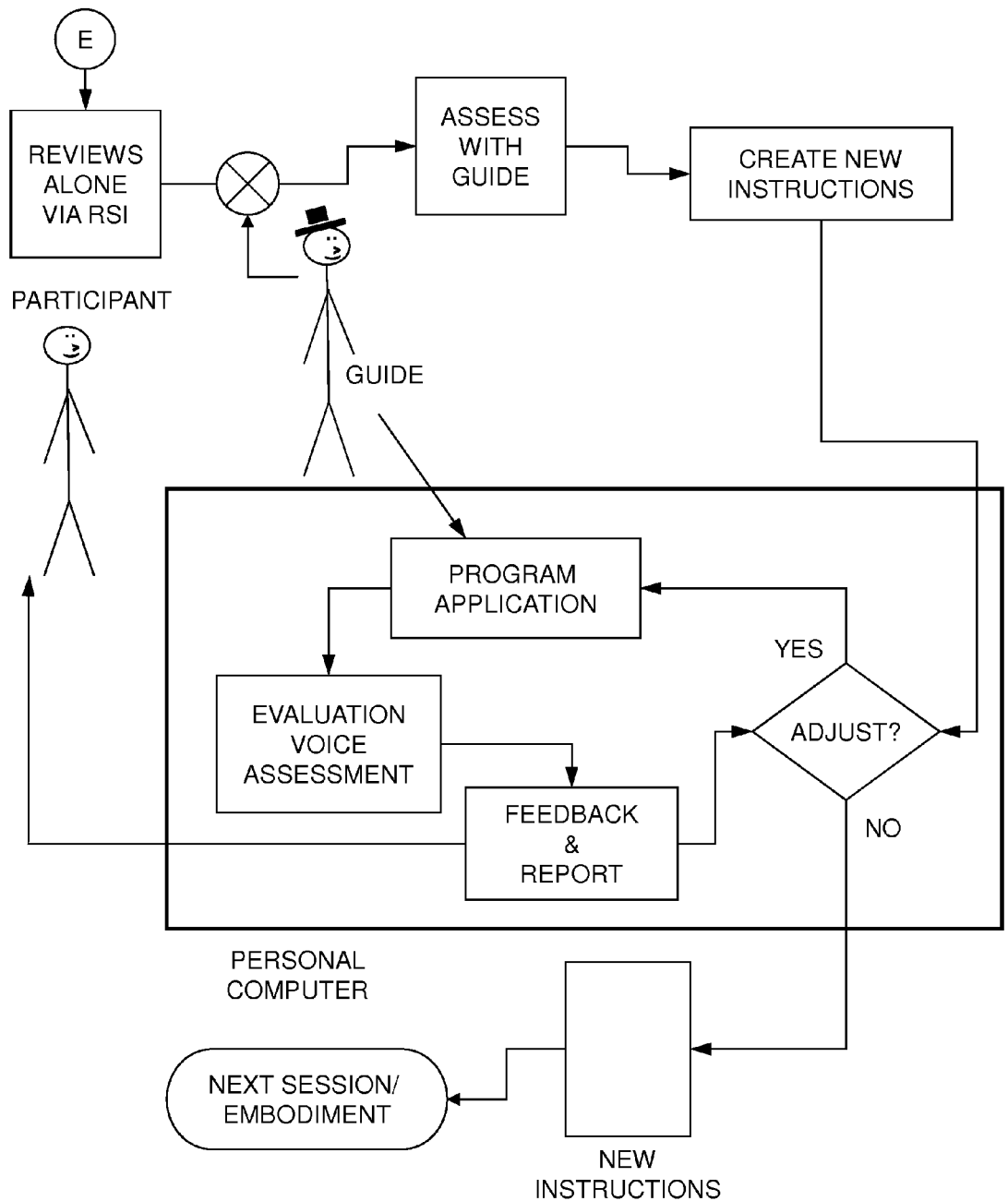

A third embodiment is shown in FIGS. 7 through 9. The following outline shows the steps taken for the third embodiment:

Embodiment III Part 1 a. Guide asks a patient for date of birth and prints a customized, blank worksheet.
b. Patient fills out worksheet.
c. Guide receives and enters past significant events and memories into application.
d. Guide asks for significance of events with slider and descriptors see FIG. 29.
e. Guide asks for most desired symptoms to resolve as a priority.
f. Guide receives the relative temperature and season that the events had occurred.
g. Guide selects a program criterion to select most likely common themes to remedy symptoms.
h. Program application outputs instruction sets based upon alternating temperatures having a bipolar bias—hot, rest, cold, rest or vice versa, presenting symptoms and themes.
i. Guide adjusts scope of instruction sets by slightly enlarging scope or adjusting parameters of the program instructions-creating-algorithm parameters.
j. Guide records patient saying brief event descriptors for audio instructions and voice analysis.

Embodiment III Part 2 a. Host sets up equipment for patient.
1. Uploads digital instructions.
2. Plays meditation music.
3. Fills tub to temperature specification.
4. Signals when tub is ready.
b. Host tests recording capabilities.
c. Host loads first instruction for patient.
d. Host explains the control panel to get next instruction, skip, end request or call for help.
e. RSI leads patient through instruction set(s) individual items.
f. RSI input from Patient on completion of each item.
g. RSI delivers next instruction.
h. RSI delivers rest break at appropriate time lapse.
i. RSI instructs patient to maintain temperature during rest.
j. RSI prompts patient to continue after rest.
k. RSI prompts host for patient's final rest.

Embodiment III Part 3 a. Voice analysis of patient before, during and after hosted session.
b. Patient reviews the recordings within 48 hours.
c. Guide receives hosted session data.
d. Program application verifies instruction integrity with temperature and patient responses.
e. Feedback reported by guide with or without the programmed assessments.
f. New session's instructions are created and any new data of historic events added or priorities adjusted as necessary.

It has a data intake the same as the second embodiment with the addition of a bipolar bias in the instruction creation. Instead of having the just one significant temperature change, it uses alternating temperatures, cold then hot or vice versa with brief rests in between the immersions. To achieve alternation, the guide or program application could overrule default reverse chronological order (if such default order did not happen to have alternating hot events and cold events). In FIG. 8 the immersion cycle is handled by the patient at the hosting site with the aid from the host to prepare the tub and load the first instruction set for the patient. The guide is not present at the hosting site. The RSI delivers the instruction sets to the patient.

FIG. 9 shows the patient alone reviewing the session performed within 48 hours. The patient also performs the voice analysis before, during and after the hosted session. Later, the guide joins the patient to verify the temperature integrity with the patient's responses. Feedback from the guide is given to the patient as well as a new instruction set created.

Figure 10:
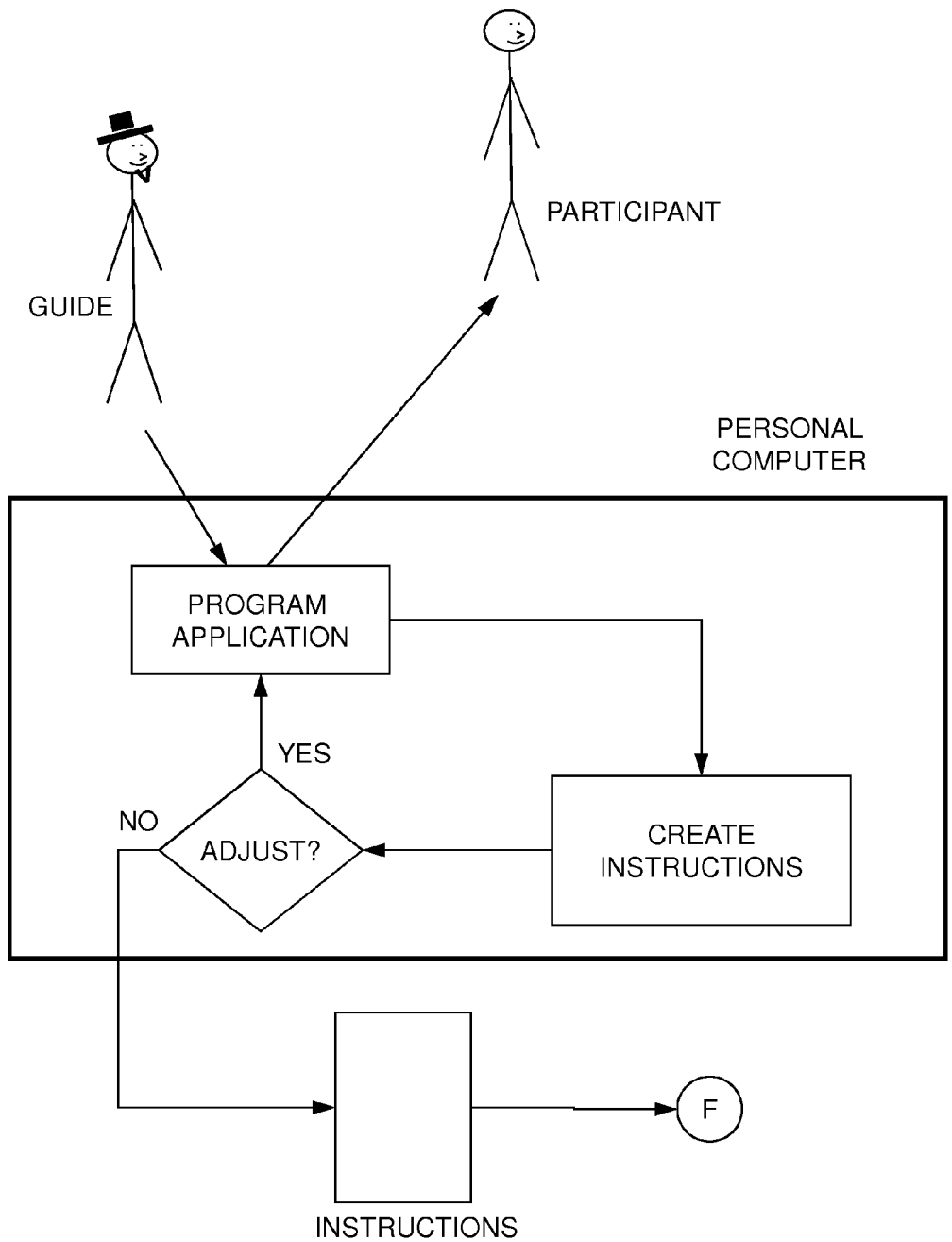
FIGS. 10 to 12 are a flowchart of a fourth embodiment that shows the guide and host assisting remotely.
Figure 11:
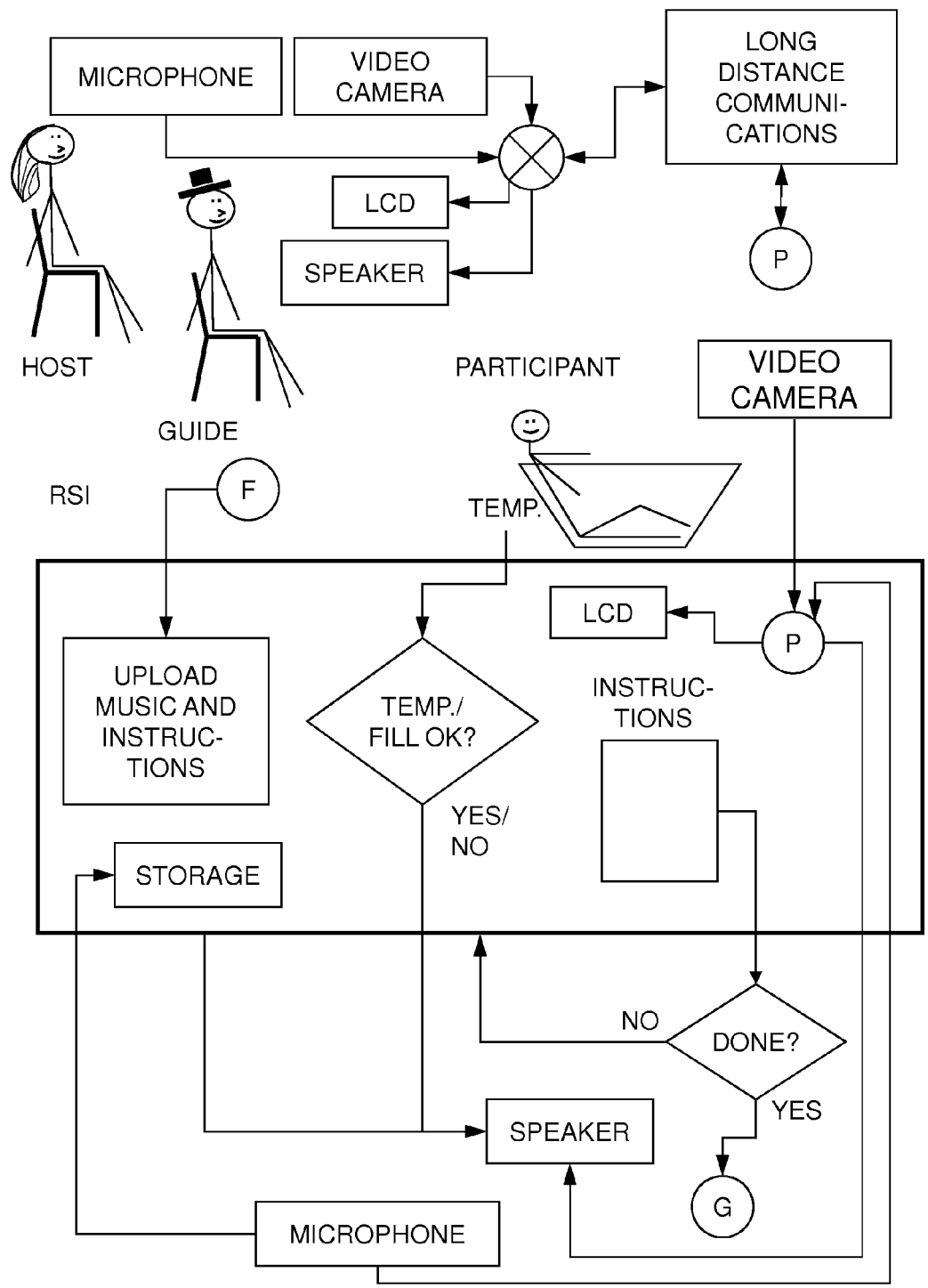
Figure 12:
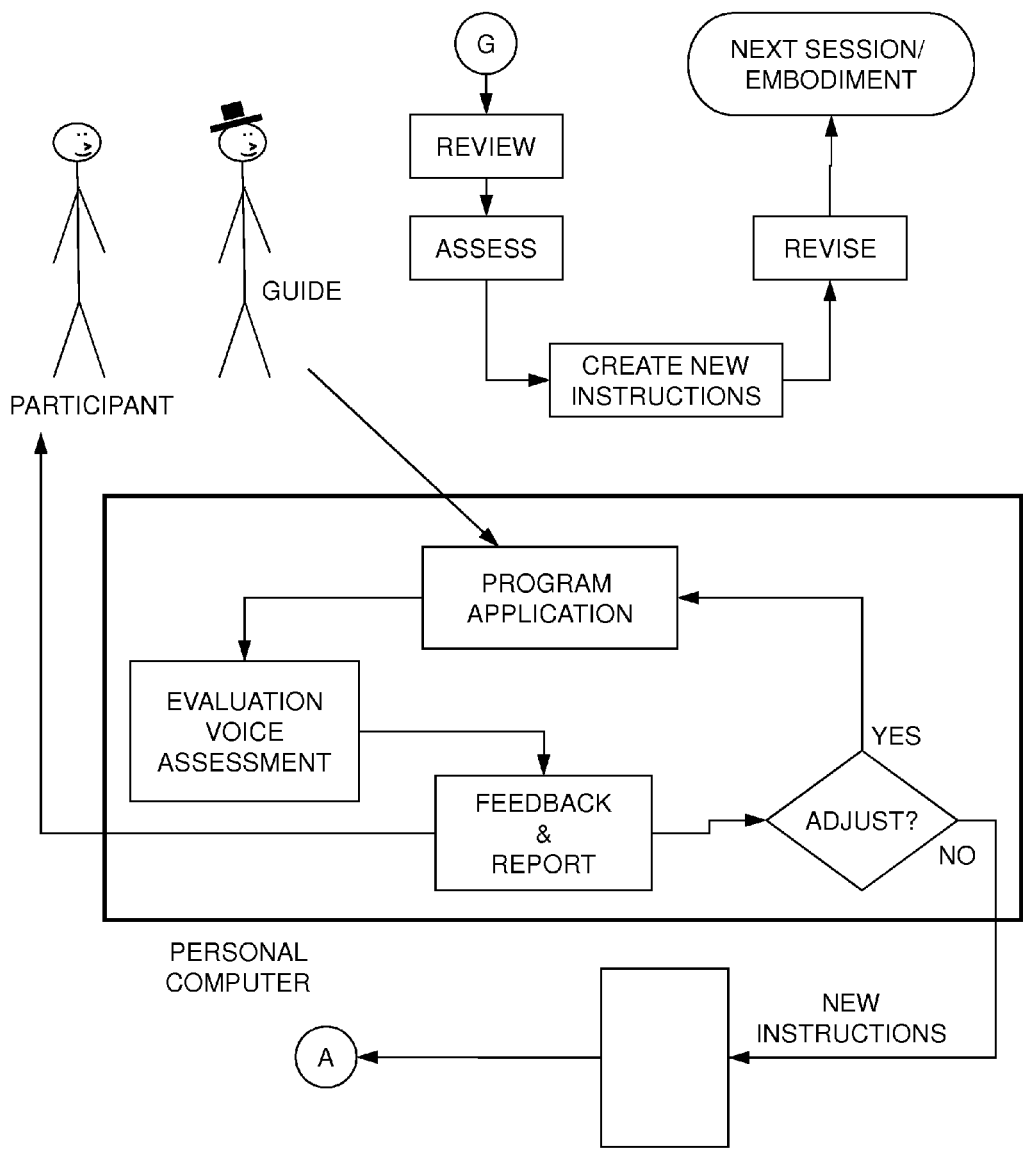

A fourth embodiment is shown in FIGS. 10 through 12. The following outline shows the steps taken for the fourth embodiment:

Embodiment IV Part 1 a. Guide asks a patient for date of birth and prints a customized, blank worksheet.

b. Patient fills out pre-printed worksheet.

c. Guide receives and enters past significant events and memories into application.

d. Guide asks for significance of events with slider and descriptors (FIG. 29).

e. Guide asks for most desired symptoms to resolve as a priority.

f. Guide receives the relative temperature and season that the events had occurred.

g. Guide selects a program criterion to select most likely common themes to remedy symptoms.

h. Program application outputs instruction sets based upon temperature, presenting symptoms and themes.

i. Guide adjusts scope of instruction sets by slightly enlarging scope or adjusting parameters of the program instructions-creating-algorithm parameters.

j. Guide records patient saying brief event descriptors for audio instructions and voice analysis.

Embodiment IV Part 2 a. Remotely Host assists set-up of equipment with patient.
 1. Uploading music and digital instructions.
 2. Playing meditation music.
 3. Directing patient to meditate.
 4. Filling tub to temperature specification on timed signal.
 5. Testing recording capabilities.
 6. Explaining the control panel to get next instruction, skip, end request or call for host or guide help.

b. Guide remotely aids data collection with patient in conjunction with the RSI.
 1. Loading first instruction with patient.
 2. Helping the emotional addressing of significant events.
 3. Encouraging patient to continue.
 4. Recommend resting and retry, or concurring to abort and reschedule.

c. RSI leads patient through instruction set(s) each individual item.

d. RSI gets input from Patient on completion of each item.

e. RSI delivers next instruction.

f. RSI delivers rest break at appropriate time lapse.

g. RSI instructs patient to maintain temperature during rest.

h. RSI prompts patient to continue after.

i. RSI prompts patient for a final rest.

Embodiment IV Part 3 a. Guide and patient review the recordings within 24 hours.

b. Guide receives hosted session data.

c. Voice analysis of patient recordings before during and after hosted session.

d. Program application verifies instruction integrity with temperature and patient responses.

e. Feedback reported by guide with or without the programmed assessments.

f. New sessions instructions are created any new data of historic events added or priorities adjusted as necessary.

The data intake is the same as the second embodiment using the custom worksheets. The guide prepares the data priorities and goals in the same manner earlier described to create the themed instruction set(s). This embodiment differs in that the host and guide participate remotely at the appointed time. Guidance is given via telephone, teleconferencing or videoconferencing via the web or suitable communication services. The web could be used in conjunction with the RSI such that text messages are sent upon completion of tasks. Tasks done during the second embodiment would be performed in this embodiment assisted remotely by the host and guide. The RSI would carry out the same tasks as in the second embodiment as well as handle additional communications required for remote assistance or communication.

FIG. 12 shows the same review process as in the second embodiment part 3, except the guide and patient review the session within 24 hours. Another difference is that the new instructions use the first embodiment for execution. This shows the versatility various embodiments can have when one leads to another, especially for training purposes or for scheduling convenience.

Variations

The system itself can be modified slightly in several ways. Temperature or other sensors can be wireless. Further sources of audio recording may be added supporting other objectives. Other microprocessor controllers from manufacturers other than Cypress Semiconductor can be substituted. Procedural steps can be adjusted also in durations for each phase can be lengthened or shortened. Also, time between phases can be adjusted to meet scheduling demands of the patient or guide availability. The components can be altered or share functions across devices; for example a hand held human interface device can be used as the session interface device by interacting with the satellite application interface, provided these devices handle between them the functions and calculations with the process steps. A more concrete example of this variation would be to use a personal phone to receive the patient's inputs and to use its speaker and or display to send guided instruction sets and it would have to interact with a storage device to record and store the patient responses.

For procedural adaptations some examples are presented. One such variation would be to have a third role added and performed by an assistant or plurality thereof to the guide and the patient, especially when they perform functions together. The assistant could handle the manual recording and the setting up of equipment. Another function could serve to buffer ethics issues that could arise in the procedure. Ethical issues could also be baked into the functions of the equipment, too. The RSI could direct audio signals of certain strength during, say phases 2 through 4, where the patient is in the rest or meditative states. While speaking ethically, one option would be for the patient to wear some type of aquatic or bathing suits especially in the presence of other roles or assistants, and the other options of being naked would most likely be performed while the patient was alone, or to enhance the significant temperature change applied to the patient. Another ethical input could be to place a microphone upon the guide and assistant and record these and store for later assessment. Furthermore, these assisting roles could be performed by another agency such as a clinical setting as a service to patient and/or guide. More specifically, and in the cases where the traumatic history may include sexual events, a system similar to buffered water massage system that would allow patient to be fully dressed and still apply a significant temperature change to their body or portion thereof could be imbedded into the procedure.

The Review phases can be separated by many days. Separating the Data Entry/Review Phase by up to a few weeks may help the patient ease into learning and practicing the procedure. This may be desired especially if they are hesitant or emotionally uncomfortable in performing it. The use of meditative music can be eliminated entirely; especially after the procedure and the skills to create the momentary stressful nature becomes well practiced. Visual recordings can be incorporated instead of or in addition to audio recordings; in using the visual aspect the patient is encouraged to revisit places of anxiety or recreate their own close approximate setting and re-enact the traumatic event solo or with the guide and other assistants if desired. The patient will be playing themselves in their original trauma. Other patient's roles can be imagined. In this way, their imagination and body positions assumed can be helpful recalling experiential memory. This visual re-enactment should be done prior to or in conjunction with the meditation and preferably in the same day that significant temperature changes is applied. Do note that there will probably require a significant set of hours to implement the re-enactment situation dealing with lighting, camera angle and rough plot and script. Also, the playback of such may be more time consuming to review because the patient requires seeing themselves in the Review Phase and the additional storage, management and possible edits or selections of the audio material in case of sharing with guide.

In addition to PTSD, phobias and achievement goals may be rectified using these procedures. Tailoring the mindset and procedure to match the phobia themes or desired goal is well suited. Similar symptoms in phobias and anxiety disorders will be suited for further adaptability in particular obsessive compulsive disorder, manic depression, dissociative identity disorder, multiple personality disorder and other anxiety disorders. Many of these presenting anxiety symptoms have an oscillating nature between reactions. Adjusting the procedure to alternate between hot and cold significant temperature changes could be a practical adaptation to minor the presenting anxieties. Further analysis of data collected between successive patient sessions having different themed instruction sets may be suitable as an extra service or means for providing better guided session instructions.

One or more embodiments have been described. Nevertheless, it will be understood that various modifications may be made. Accordingly, other embodiments are within the scope of the following claims.

I claim:

1. A system comprising one or more processors, memory and/or storage, said one or more processors, memory and/or storage containing programming instructions for the system to:
   receive a participant's history of emotional events;
   arrange the events in sets of common themes;
   create directions sets to guide the participant;
   print or send the directions to an application for the participant's usage;
   receive sensed temperature data for a tub;
   deliver directions identifying particular said emotional events of the participant; and
   control a temperature of the tub to correspond to respective temperatures associated with the emotional events,
wherein the system further comprises an interface device having:
   a single or plurality of sensors to measure said temperature data for the tub;
   a single or plurality of sound devices to play and record audio signals; and
   a single or plurality of input sensors and outputs of the directions to interact with the participant regarding steps completed and the directions given,
wherein the program instructions further provide for the system to:
   record the participant's experience and observations of their body's reactions;
   play background meditative music;
   direct the participant to immerse in the tub of water having a significant temperature difference to the participant's normal body temperature;
   direct the participant to re-live the emotional events;
   direct the participant to rest from the exposure to the temperature change for a period of time;
   and
   direct the participant to rest for a final period from one minute to about 60 minutes.

* * * * *